United States Patent [19]

Amundsen et al.

[11] Patent Number: 4,702,108
[45] Date of Patent: Oct. 27, 1987

[54] METHOD AND APPARATUS FOR MEASURING THE ISOMETRIC MUSCLE STRENGTH OF MULTIPLE MUSCLE GROUPS IN THE HUMAN BODY

[75] Inventors: Louis R. Amundsen, New Brighton; Robert P. Patterson, St. Anthony; Tanya L. Baxter, Minneapolis; Glenn N. Scudder, Edina; Wayne O. Duescher, Roseville; Willis E. Dahlman, Cambridge; Gary W. Schukar, White Bear Lake; Clarence I. Steinback, Edina, all of Minn.

[73] Assignees: Regents of the Univ. of Minnesota, Minneapolis; Twin City Surgical, Inc., St. Paul, both of Minn.

[21] Appl. No.: 825,851

[22] Filed: Feb. 4, 1986

Related U.S. Application Data

[63] Continuation-in-part of Ser. No. 748,088, Jun. 24, 1985, abandoned.

[51] Int. Cl.⁴ .............................................. A61B 5/22
[52] U.S. Cl. ..................................... 73/379; 272/125; 272/134
[58] Field of Search ......................... 73/379; 128/774; 272/125, 134

[56] References Cited

U.S. PATENT DOCUMENTS

| | | |
|---|---|---|
| 3,285,070 | 11/1966 | McDonough . |
| 3,374,675 | 3/1968 | Keropian . |
| 3,752,144 | 8/1973 | Weigle, Jr. . |
| 4,236,528 | 12/1980 | Stanec et al. . |
| 4,256,302 | 3/1981 | Keiser et al. . |
| 4,333,340 | 6/1982 | Elmeskog . |
| 4,354,676 | 10/1982 | Ariel . |
| 4,363,480 | 12/1982 | Fisher et al. . |
| 4,423,630 | 1/1984 | Morrison . |
| 4,425,797 | 1/1984 | Morrison . |
| 4,452,447 | 6/1984 | Lepley et al. . |
| 4,462,252 | 7/1984 | Smidt et al. . |
| 4,463,946 | 8/1984 | Wallace et al. . |
| 4,469,325 | 9/1984 | Ware . |
| 4,471,957 | 9/1984 | Engalitcheff, Jr. . |
| 4,475,408 | 10/1984 | Browning . |
| 4,493,485 | 1/1985 | Jones . |
| 4,501,148 | 2/1985 | Nicholas et al. . |

FOREIGN PATENT DOCUMENTS 2912981 10/1980 Fed. Rep. of Germany .

OTHER PUBLICATIONS

Isotechnologies, Inc.: re the Isostation (TM) A-100 (brochure).
Isotechnologies, Inc.: re the Isostation (TM) B-100 (brochure).
Biokinetic Fitness Laboratories, Inc.: re Biokinetic Modular Therapy System, Product News, vol. 65, No. 3, Mar. 1985.
Biodex Corporation: re the Biodex system (brochure).

(List continued on next page.)

*Primary Examiner*—Charles A. Ruehl
*Attorney, Agent, or Firm*—Merchant, Gould, Smith, Edell, Welter & Schmidt

[57] ABSTRACT

An apparatus and method for isometric muscle strength testing using a chair apparatus (40) having a support frame structure (42), a seat assembly (46), a foot rest assembly (60) and load cells (100) interconnected to the support frame structure (42) for measuring the isometric force exerted by any of a plurality of muscle groups in a human subject's body. The load cells (100) are possibly positioned on six track systems; a posterior track (80a), left and right lateral tracks (80b,c) an anterior track (80d), a forward upper track (80e) and a forward lower track (80f) to enable alignment with the muscle group selected for testing. A thorax restraint assembly (120), a sacral pad assembly (140), a pelvic restraint assembly (150), a thigh restraint assembly (160) and a calf restraint assembly (170) are present for selectively engaging and immobilizing parts of the human subject's body, including the pelvis, thorax, thighs and legs, as required to enable the muscle group selected for testing to be tested while isolated from the other muscle groups of the human subject's body.

13 Claims, 46 Drawing Figures

OTHER PUBLICATIONS

Biodex Corporation: Comparative Feature Chart (brochure).

Chattecx Corporation: brochure re the "KIN-COM" System.

MGI Strength/Fitness Systems: brochure re exercise/therapy systems.

Cardon Rehabilitation Products: brochure re exercise and medicine training therapy systems.

Wilson Fitness Systems: brochure re Wilson (R) ARIEL 4000 computerized exercise system for use in sports medicine, etc.

Hydra-Fitness: brochure re the Omni-Tron System I.

Biokinetic Data Acquisition: paper by Nort Thornton and Evan R. Flavell titles "The Computer Invades the Weight Room" no date.

Biokinetic Fitness Laboratories: brochure re FITLAB Inc.

Biokinetics-brochure titled "When Performance Counts".

Ariel 4000 Series-Computerized Exercise Systems by Computer Biomechanical Analysis, Inc. (multi-page brochure re ARIEL 4000).

Chattecx Corporation: brochure on the "KIN-COM" system.

Loredan: brochure re the "LIDO" system.

Spark Instruments & Academics, Inc.: brochure for hand-held dynamometers.

Norsk Sequence Training System-brochure by Chattecs Corporation.

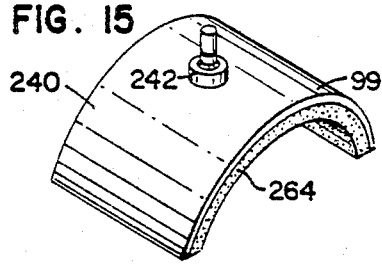
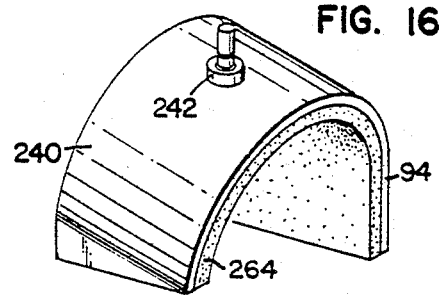
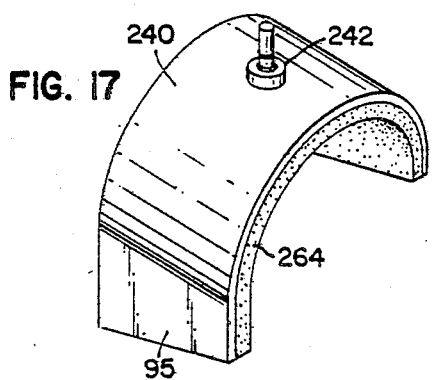
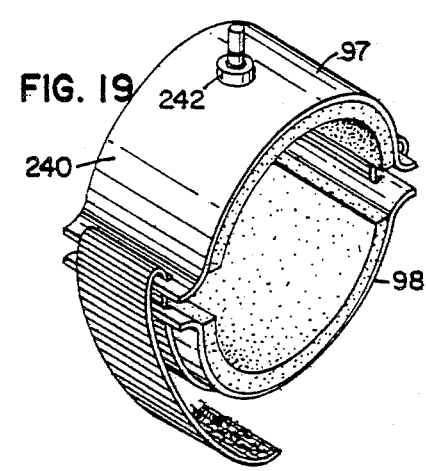
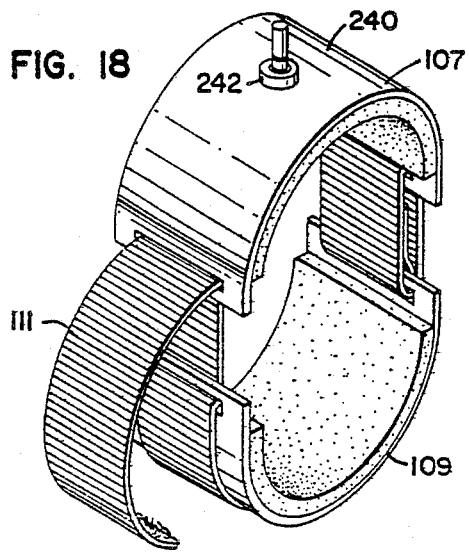
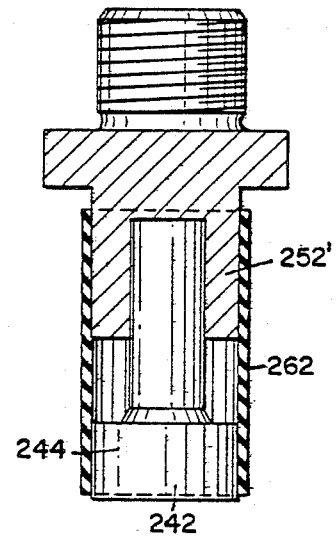

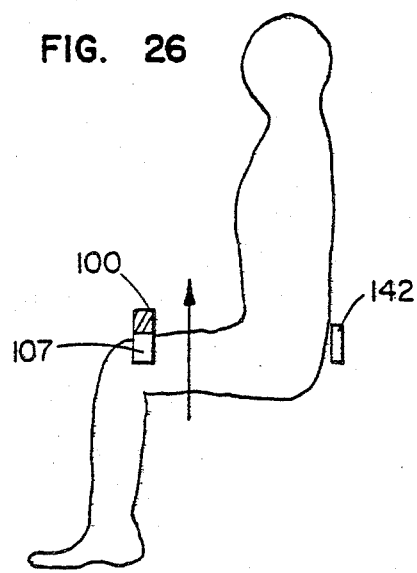
FIG. 26
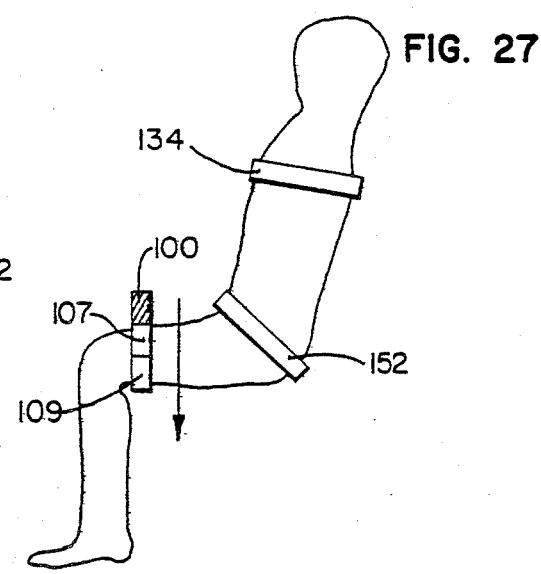
FIG. 27
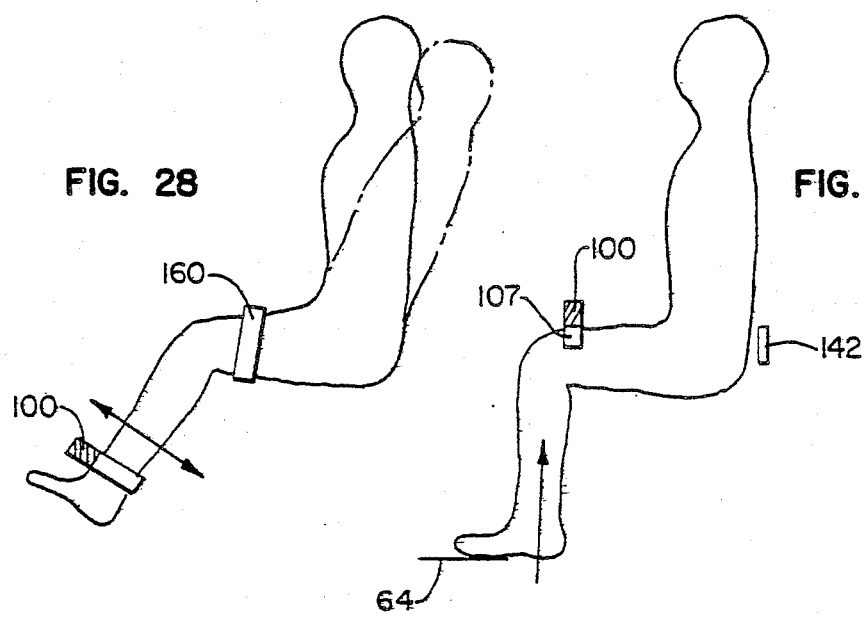
FIG. 28
FIG. 29

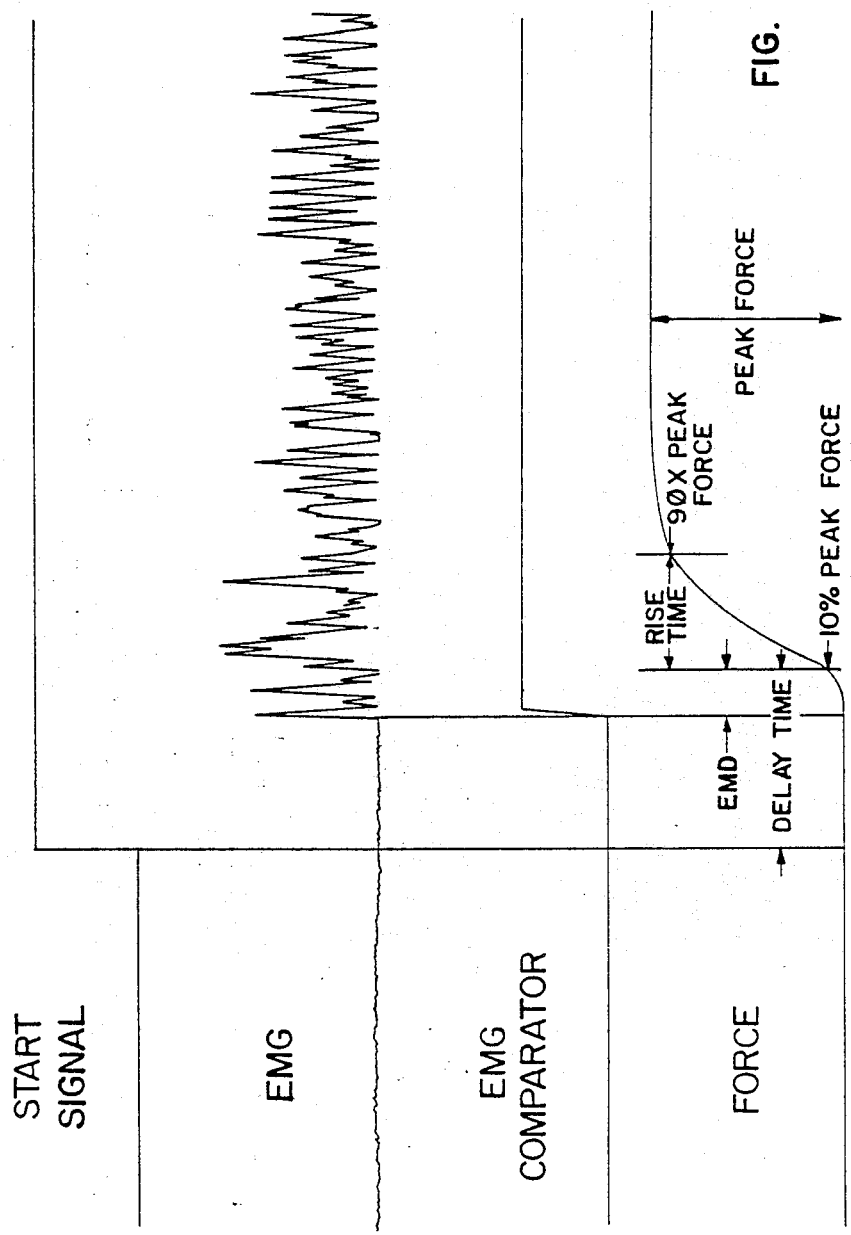

FIG. 36

PATIENT'S NAME: JOHN DOE  
AGE: 34  
WEIGHT = 222 LBS.   100.9 KG.  
HEIGHT = 55 IN.   139.7 CM.  
DIAGNOSIS-NORMAL  
HOSPITAL NUMBER: 1234  
DATE OF THE EXPERIMENT: 06/24/85

SEX: M

MUSCLE FUNCTION TESTED: HANDGRIP – RIGHT SIDE  
TIME OF THE EXPERIMENT: 3:46 P.M.  
DURATION OF EACH TRIAL = 4 SECS.  
REST BETWEEN TRIALS   = 4 SECS.  
WORKING HEART RATE    = 117/MIN.

| TRIAL NUMBER | 1 | 2 | 3 | 4 | 5 |
|---|---|---|---|---|---|
| DELAY TIME (SEC) | .164 | .328 | .234 | 0 | 0 |
| RISE TIME (SEC) | .671 | .335 | .453 | 0 | 0 |
| PEAK TIME (SEC) | 1.437 | 1.062 | 1.226 | 0 | 0 |
| PEAK FORCE (LB) | 211.7 | 199.9 | 189.4 | 0 | 0 |
| PEAK F/BODY WT. | .95 | .9 | .85 | 0 | 0 |
| AVG. FORCE (LB) | 174.8 | 170.7 | 135.1 | 0 | 0 |
| AVG. F/BODY WT. | .78 | .76 | .6 | 0 | 0 |
| E.M.D. TIME (SEC) | .030 | .035 | .032 | 0 | 0 |

SUMMARY OF THE TEST

| MUSCLE TESTED AND SIDE | MAX.FORCE | MAX F/BDWT | AVG.FORCE | AVG.F/BDWT |
|---|---|---|---|---|
| HANDGRIP--R | 211.7 | .95 | 174.8 | .78 |

FLOW CHART OF MAXIMUM STRENGTH TEST

METHOD AND APPARATUS FOR MEASURING THE ISOMETRIC MUSCLE STRENGTH OF MULTIPLE MUSCLE GROUPS IN THE HUMAN BODY

This invention was made, in part, with Government support under Grant No. G008300075 awarded by the National Institute for Handicapped Research of the Department of Education. The Government has certain rights in this invention.

This is a continuation-in-part of Ser. No. 748,088, filed June 24, 1985, now abandoned.

BACKGROUND OF THE INVENTION

The present invention relates to a method and apparatus for measuring and recording the isometric muscle strength of many if not all of the major skeletal muscle groups in the human body. More particularly, the present invention relates to a chair apparatus and method of using the same, providing for testing of multiple major skeletal muscle groups at a single test station.

Muscle strength can be defined as the ability of a muscle or group of muscles to produce tension or exert force through the human skeletal system. The muscle may contract in three different ways: (1) concentrically (force is generated while the muscle is shortening in length); (2) eccentrically (force occurs while the muscle is being elongated; and (3) isometrically (force is generated by a muscle whose length is not changing).

The generally accepted measurement criterion for the maximum tension which can be exerted by a muscle is the maximum amount of force a muscle can exert on a body part. This is referred to as the maximum strength of the muscle and might be expressed, for example, in kilograms per square centimeter of transverse section. Strength measurements should be taken at a proportional distance from the axis of rotation of the body part when comparing measurements from different subjects. This is particularly important when the force exerted by the body part is the parameter to be measured. With respect to this methodology, moment measurements should also be taken at a proportional distance from the axis of rotation.

Muscle strength testing devices typically utilize a rotating input shaft. If concentric, eccentric and/or isometric strength is to be measured, an accurate positioning of the axis of rotation of the rotating input shaft of the apparatus taking the measurement with the actual center of rotation of the body segment being assessed is required. Reasonably adequate placement has been achieved by a significant number of currently available muscle strength testing devices for testing the knee. A widely used device for measuring strength and endurance of human muscles is the Cybex II apparatus, which is described in various materials and in U.S. Pat. No. 3,465,592. However, as discussed above, this device requires that the axis of rotation of the rotating input shaft of the apparatus taking the measurement be aligned with the anatomical center of rotation of the body segment being assessed.

A recently issued patent (U.S. Pat. No. 4,462,252) describes a method and apparatus for measuring the strength of the flexors and extensors of the trunk; however, this device measures the muscle strength and endurance for only this one part of the body. This device and other devices are designed to measure concentric and often eccentric strength with the incidental ability to assess isometric strength. The complex and bulky speed control/load cell mechanisms required to test concentric and eccentric strength are difficult, if not impossible, to move from one skeletal muscle group site to another and assure proper alignment therewith so as to enable testing of multiple muscle groups at a single device or testing station.

Additionally, the muscle groups to be tested must be isolated from muscle groups which may contribute a moment of force to the apparatus measuring the muscle groups. Accordingly, the human subject must be positioned appropriately and the parts of the body containing muscles which are not part of the measurement must be stabilized or immobilized.

Prior art devices have typically not been capable of providing adequate stabilization of body parts not being tested and/or of appropriately aligning force measuring components for most if not all of the major muscle groups of the body at a single device or station. In some cases, individual devices may adequately stabilize the subject and align the device for a single or limited number of muscle groups, but these devices are not capable of appropriate stabilization and alignment for most if not all of the major muscle groups of the human body.

The present invention solves these and many other problems associated with prior muscle strength and endurance testing devices.

SUMMARY OF THE INVENTION

The present invention relates to an isometric muscle strength testing chair apparatus for measuring the isometric muscle strength of any of a plurality of muscle groups in a human subject's body. The chair apparatus includes a support having a seat assembly and a foot rest assembly mounted thereon. The chair apparatus includes stabilization means for selectively engaging and immobilizing various parts of the human subject's body, including the pelvis, thorax, thighs and legs as required to enable each of the muscle groups selected for testing to be tested while being isolated from the other muscle groups of the human subject's body. The chair apparatus further includes transducer means for measuring the force exerted by the muscle groups selected for testing, the transducer means remaining substantially stationary while the muscle groups selected for testing exert a force thereon so as to provide for isometric strength testing. Track means enables the transducer means to be adjustably positioned in association with the muscle groups selected for testing.

The present invention also relates to a method for measuring isometric muscle strength of any of a plurality of muscle groups in a human subject's body. The method includes the step of seating the human subject in a chair apparatus having a seat assembly and foot rest assembly. Various parts of the human subject's body including the pelvis, thorax, thighs and legs are selectively immobilized as required for isolating the muscle groups being tested from the other muscle groups. Transducer means is adjustably positioned in substantially stationary association with the muscle groups selected for testing. Force is isometrically applied to the transducer means by the muscles selected for testing. The transducer means generates an output signal in response to the isometrically applied force. This signal is monitored to provide an indication of the isometric muscle strength.

A primary object of this invention is to provide a method and apparatus for measuring the isometric muscle strength of most if not all of the major skeletal muscle groups in the human body. In a preferred embodiment, a computer controlled system is utilized for measuring isometric muscle contractions by use of a suitable transducer, such as tension/compression load cells.

An object of an embodiment of this invention is to provide a method and apparatus for isometric muscle endurance testing as well as strength testing. Yet another object of an embodiment of this invention is to provide a method and apparatus for isometric exercise training.

A further object of yet another embodiment of the present invention is to store the muscle strength data collected and perform further processing thereon and/or transfer the processed and/or unprocessed data to a local client data base and/or a central computer.

It is another object of this invention to provide a patient or subject stabilization chair apparatus which effectively isolates individual muscle-joint actions from other parts of the subject's body to enable measuring and recording of isometric muscle strength and endurance. The following are examples of muscle-joints or muscle groups of the human body:

(1) Elbow flexion
(2) Elbow extension
(3) Shoulder flexion
(4) Shoulder extension
(5) Shoulder abduction
(6) Shoulder adduction
(7) Shoulder internal rotation
(8) Shoulder external rotation
(9) Hip flexion
(10) Hip extension
(11) Hip abduction
(12) Hip adduction
(13) Knee flexion
(14) Knee extension
(15) Ankle plantar flexion
(16) Ankle dorsiflexion
(17) Spine The spine can be further separated into the following actions:
(1) Trunk
  (a) Flexion
  (b) Extension
  (c) Lateral bending (right and left)
(2) Neck
  (a) Flexion
  (b) Extension
  (c) Lateral bending (right and left)

It is a further object of the present invention to provide a strength testing system which permits the accurate measurement of isometric strength by accurately positioning the load cell devices a known appropriate distance on the center of rotation and perpendicular to the direction of force being exerted by the appropriate skeletal part of the body.

It is also an object of one embodiment of this invention to provide signal generation and conditioning by compression/tension load cells, such as 500 and 1,000 pound load cells, models SM-500 and SM-1000, respectively; an analog to digital signal conversion system, a personal computer such as an Apple IIE, and appropriate computer programs for measuring isometric muscle strength and endurance.

It is an object of yet another embodiment of this invention to provide computer controlled data collection, analysis and storage for a series of factors relating to time intervals, maximum force, force decrement over time and the smoothness of the force curve, which describes isometric muscle strength and endurance.

It is an object of the present invention to provide an apparatus for stabilizing the subject and for mounting and positioning load cells. In one embodiment, the apparatus consists of a framework which supports a seat which can be moved forward and backward, a foot rest which can be adjusted up and down, strap stabilization devices and tracks for the adjustable placement of load cells. Strap restraining devices are utilized to stabilize the pelvis, thighs, legs and thorax as needed for specific muscle-joint actions. This enables specific muscle-joint actions and thereby muscle groups to be tested rapidly and in isolation.

In one embodiment, it is an object to provide an apparatus for stabilizing the subject which includes six track systems which are used for placement of the load cells:

(1) Posterior Track. The load cell which is used to measure trunk extension and neck extension strength and endurance is mounted on the posterior track.

(2) and (3) Left and Right Lateral Tracks. One load cell is mounted on each of these tracks. These load cells are used to measure lateral bending of the trunk and neck and shoulder abduction and shoulder adduction strength and endurance.

(4) Anterior Track. One load cell is mounted on this track to measure trunk and neck flexion strength and endurance.

(5) Forward Upper Track. This track allows load cell movement laterally, forwardly along the thigh and up and down to the foot and ankle. This track system allows the measurement of ankle plantar and dorsiflexion, hip flexion and extension, hip abduction and adduction, hip rotation (internal and external), elbow flexion and extension, shoulder flexion and extension and shoulder rotation (internal and external) strength and endurance.

(6) Forward Lower Track. One load cell is mounted on this track to measure knee flexion and extension strength and endurance.

It is an object of the present invention to enable rapid measurement of isometric muscle strength which generally profiles the major muscle groups in the human body.

In one embodiment of the present invention, it is an object to provide categorizing of amplitude and temporal factors, including measurement of EMG and parameters related to the timing of the EMG with respect to the force response. In addition to other advantages, this allows for the possible determination of muscle fiber type and fatigue characteristics.

It is an object of the present invention to better quantify a patient's motor ability and provide diagnostic information.

It is yet another object of the present invention to provide a method and apparatus of the present invention at a relatively low cost and in a form which is semi-transportable.

In addition, it is an object of one embodiment of the present invention to provide a single station for testing of the various muscle groups of the human body and which is adjustable to fit many different sizes of individuals.

It is a further object of one embodiment of the present invention to provide for diagnosis of muscular diseases. One embodiment of the present invention can be used with very weak people, since the slightest amounts of force can be measured, unlike that of conventional cable and chair systems, which require several pounds of force just to take up slack in the system.

It is an object of yet another embodiment of the present invention to provide a computerized system which can record the information received and feed that information into a client information data base, as well as provide hard copy printouts of the test results.

It is an object of one embodiment of the invention to utilize axially loaded load cells as the transducer apparatus for converting isometric muscle force into an electrical signal, thereby eliminating the need for rotating input shafts required in eccentric/concentric strength testing. However, lever arm lengths can be measured thereby enabling torques to be determined by the invention.

These and various other advantages and features of novelty which characterize the present invention are pointed out with particularity in the claims annexed hereto and forming a part hereof. However, for a better understanding of the invention, its advantages and objects attained by its use, reference should be had to the drawings which form a further part hereof and to the accompanying descriptive matter and in which there is illustrated and described an embodiment of the invention.

BRIEF DESCRIPTION OF THE DRAWINGS

In the drawings, in which like reference numerals and letters indicate corresponding parts throughout the several views.

FIG. 14 is an alternate embodiment of the attachment apparatus illustrated in FIG. 13;

FIGS. 15 through 19 are perspective views of embodiments of various cuff apparatus in accordance with the principles of the present invention;

FIGS. 26 through 33 are diagrammatic drawings illustrating testing of various muscle groups;

FIG. 35 is a graph of various input parameters in accordance with the principles of the present invention;

FIG. 36 is a sample printout obtained upon completion of muscle strength testing;

A DETAILED DESCRIPTION OF THE PREFERRED EMBODIMENTS OF THE INVENTION

Figures 1, 2:
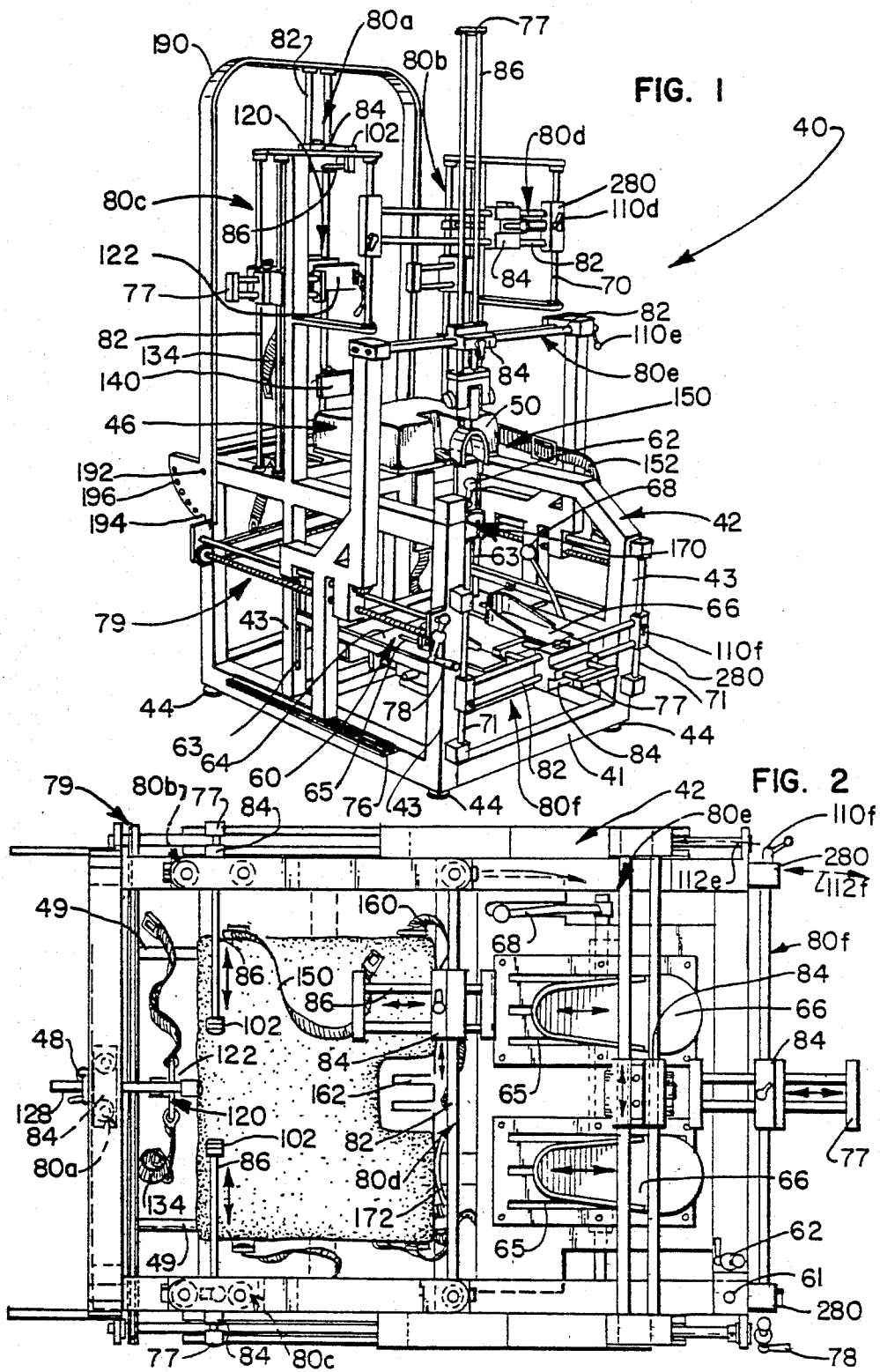
FIG. 1 is a view in perspective of an embodiment of the chair apparatus in accordance with the principles of the present invention.
FIG. 2 is a view of the embodiment shown in FIG. 1, as seen generally from the top.

Referring now to the Figures, there is illustrated in FIG. 1 an embodiment of a chair apparatus, generally identified by the reference numeral 40, in accordance with the principles of the present invention. As illustrated in FIG. 1 and additionally in FIGS. 2 through 6, the embodiment of the chair apparatus 40 illustrated includes a support frame structure 42 mounted on four adjustable foot pads 44. The chair apparatus 40 further includes a seat assembly 46 for seating of the patient or subject to be tested. The seat assembly 46 is horizontally adjustable in a forward and a backward direction with respect to the subject by operation of a crank 48 on a rear side of the chair apparatus 40, roughly in the center, just below a seat pad 50 of the seat assembly 46. Turning the crank 48 causes a screw rod assembly 47 to which the seat assembly 46 is interconnected to turn, thereby causing the seat assembly 46 to slide along two cylindrical rods 49 on which the seat assembly 46 is slidably mounted. The embodiment of the chair apparatus 40 shown further includes a foot rest assembly 60 positioned generally forwardly of and downwardly from the seat assembly 46. The foot rest assembly 60 is vertically adjustable by use of a crank 62 on a right side of the chair apparatus 40 which causes a vertical screw rod assembly 61 interconnected to the foot rest assembly 60 to turn, thereby causing the foot rest assembly 60 to move vertically along slots 63 in the support frame.

In the embodiment of the chair apparatus 40 shown in FIGS. 1 through 6, the foot rest assembly 60 includes a platform 64 which is raised and lowered by the crank 62 and two foot plates 66 positioned in slots 65 of the platform which can be adjustably positioned forward, backward and/or pivoted to a more comfortable position. This is accomplished by loosening the footplates 66 by use of a lever 68 on a left side of the chair apparatus 40. The footplates 66 are locked in place by pushing the lever 68 backwardly and downwardly.

As shown in FIGS. 1 through 6, the chair apparatus 40 includes six track systems which enable placement of load cells at any number of specific locations. As illustrated, the six track systems present include a posterior track 80a at the back of the chair apparatus 40, left and right lateral tracks 80b, 80c generally along the left and right sides of the chair apparatus 40, respectively, an anterior track 80d extending generally across in front of the chair apparatus 40, a forward upper track 80e positioned slightly in front of and below the anterior track 80d and a forward lower track 80f positioned below and in front of the forward upper track 80e. The forward upper track 80e is adjustably mounted for horizontal movement on a crank and chain assembly 79 such that by use of a crank 78 on the left side of the chair apparatus 40, the forward upper track 80e can be moved forwardly and backwardly of the subject seated in the chair. Channel members 76 provide support for the forward upper track 80e as it slides along. The anterior track 80d and the forward lower track 80f are mounted on frame members 70, 71, respectively, by mounting attachments 280 which enable vertical adjustment of the tracks 80d and 80f along the members 70, 71.

Figure 7:
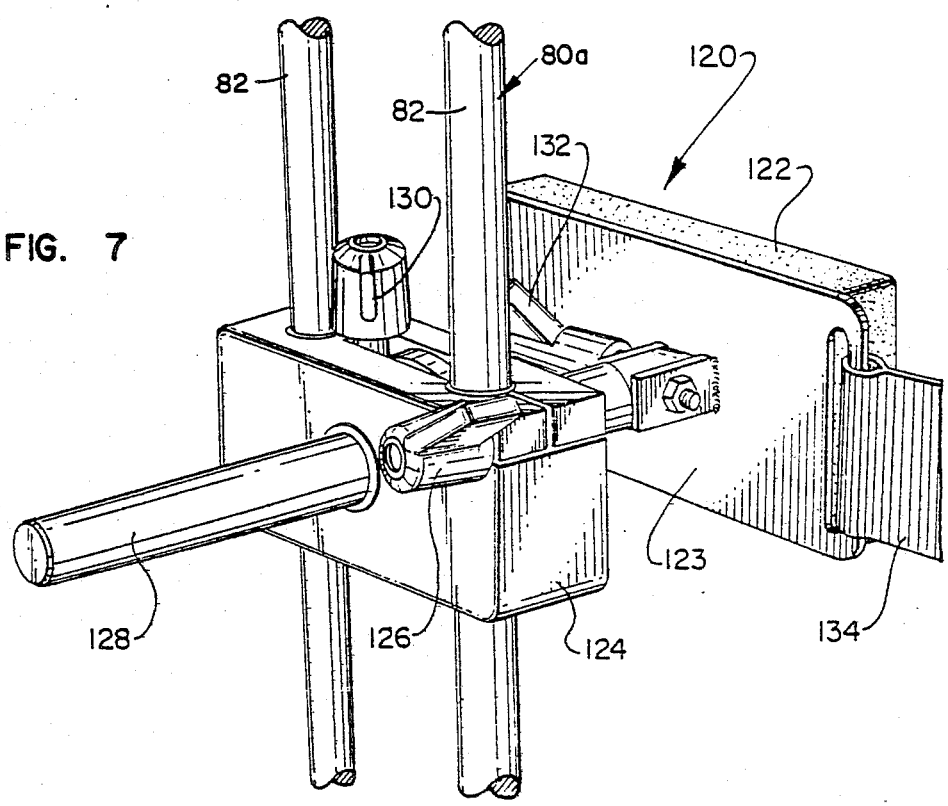
FIG. 7 is an enlarged perspective of an embodiment of a thorax restrain assembly in accordance with the principles of the present invention.
Figure 8:
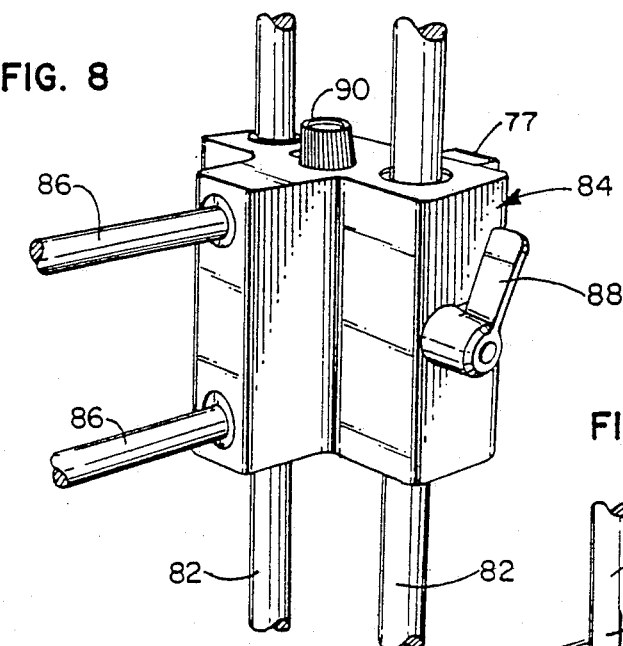
FIG. 8 is a perspective view of an embodiment of a T-block apparatus in accordance with the present invention.
Figure 9:
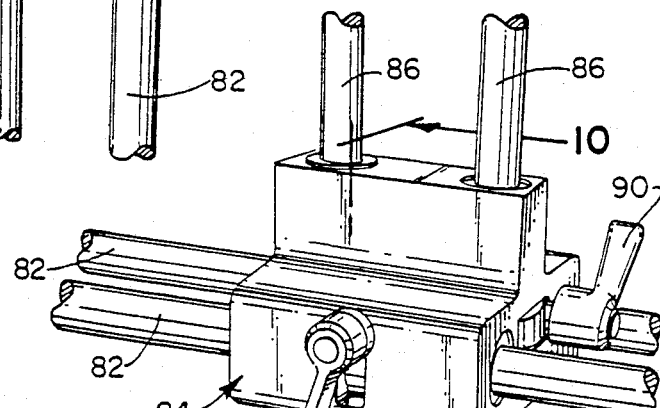
FIG. 9 is a perspective view of an embodiment of a pivotal mounting assembly interconnected to an embodiment of a T-block assembly, as shown in FIG. 8.

As illustrated in FIGS. 1 through 6, and more particularly in FIGS. 7 through 9, each of the track systems includes two cylindrical rods 82 such as Thompson rods mounted in a parallel, spaced apart relationship. Slidably positioned on the rods 82 is a T-shaped block 84 having two cylindrical bores with linear bearings adapted for slidable receipt of the rods 82. The T-shaped block 84 includes two parallel, spaced apart cylindrical bores extending perpendicular to the rods 82 and similarly adapted to slidably receive rods 86. The rods 86 are capable of being slid through the T-shaped block 84 in a direction generally perpendicular to that of the rods 82. The rods 86 provide for mounting of load cells and other suitable end attachments at the end of the rods 86. The T-shaped blocks 84 in turn include a lever or latch 88 for locking the T-shaped blocks 84 in position on the rods 82 and for unlocking the same to enable adjustable positioning of the T-shaped blocks 84 along the rods 82. In addition, the T-shaped blocks 84 include a lever or latch 90 which similarly enables tightening and loosening of the rods 86 with respect to the T-shaped blocks 84. Positioned at an outer end of the rods 86 is a hand grip member 77 which the user can grasp when sliding the rods 86 back and forth. Accordingly, the track systems enable positioning of load cells for purposes of isometric muscle strength and endurance measurements at any number of specified locations wherein most, if not all, of the major skeletal muscle groups of the human body can be tested.

Figure 10:
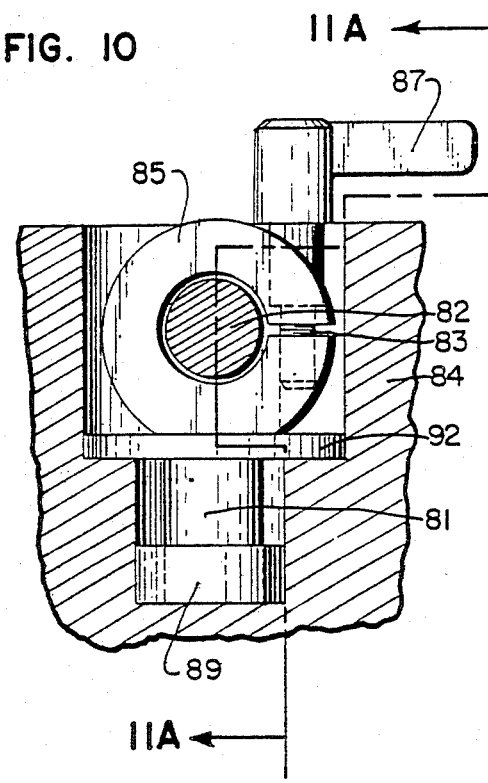
FIG. 10 is a view as seen generally along the line 10—10 in FIG. 9.
Figure 11A:
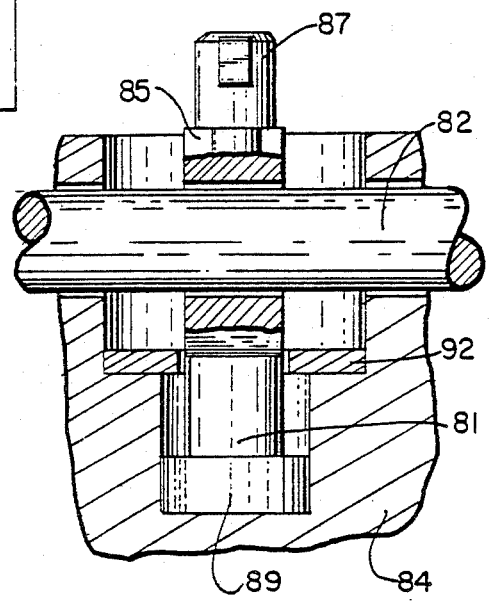
FIG. 11A is a cross-sectional view of the embodiment shown in FIG. 10.
Figure 11B:
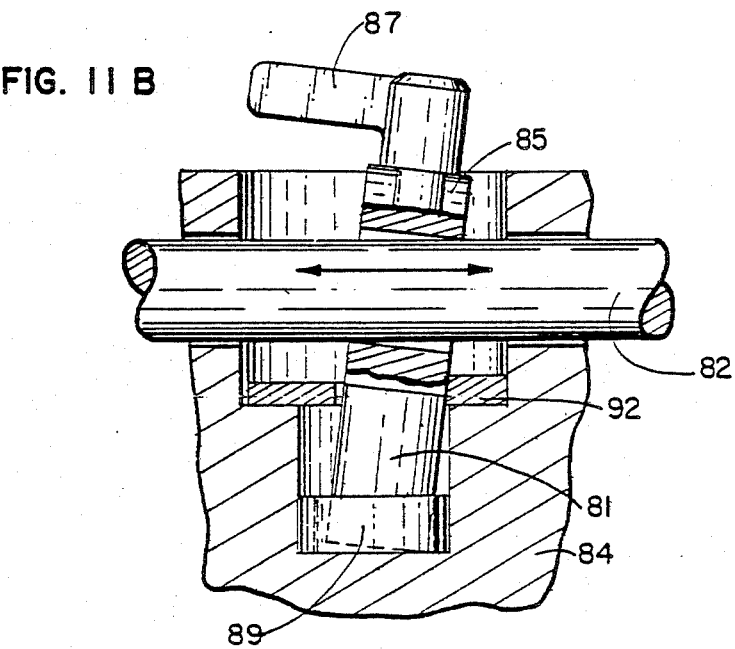
FIG. 11B is a view similar to FIG. 11A with the latch in the locked position.

As illustrated in FIGS. 10 and 11A,B, the latch or lever 88 includes a handle portion 87 interconnected to a split locking collar 85 by a threaded member 83. The threaded member 83 interconnects ends of the split locking collar 85. In addition, the split locking collar 85 is interconnected to an elongated pedestal member 81 roughly the width of the locking collar. The pedestal member 81 is anchored at its lower end by a collar member 89 which is spaced from the pedestal member 81 to enable the pedestal member 81 to tilt or cant when force is applied. The split locking collar 85 is stabilized and centered by an elastic, rubber-like collar member 92 in an opening of the T-shaped block 84 so as to allow space on either side of the locking collar 85 and allow the cylindrical rod 82 to slide through the locking collar. By turning the handle 87 of the latch 88, the threaded member 83 cooperates with the split locking collar 85 to increase or decrease the inside diameter of the split locking collar 85. In a released position, the locking collar 85 has an inside diameter which is slightly greater than that of the cylindrical rods 82 such that the T-shaped block 84 readily slides therealong. When tightened a quarter turn, the inside diameter of the locking collar 85 is decreased so as to engage the cylindrical rod 82. The locking collar 85 is canted by the effect of the movement of the cylindrical rod 82 such that the locking collar 85 wedges against the cylindrical rod 82 so as to prohibit movement of the T-shaped block 84 relative to the cylindrical rod 82. The load imparted on the locking collar 85 by the cylindrical rod 82 is transferred by the pedestal member 81 to the load reaction collar member 89 as the collar member 89 engages the bottom of the pedestal member 81 as it tilts or cants with the locking collar 85. It will be appreciated that the lever 88 thus provides a mechanism for loosening and tightening the T-shaped block 84 which does not require a lot of force or effort to be exerted on the handle portion 87. Indeed, the more force applied to the cylindrical rod 82, the more wedging will occur between the locking collar 85 and the cylindrical rod 82 when in a tightened position.

Figure 13:
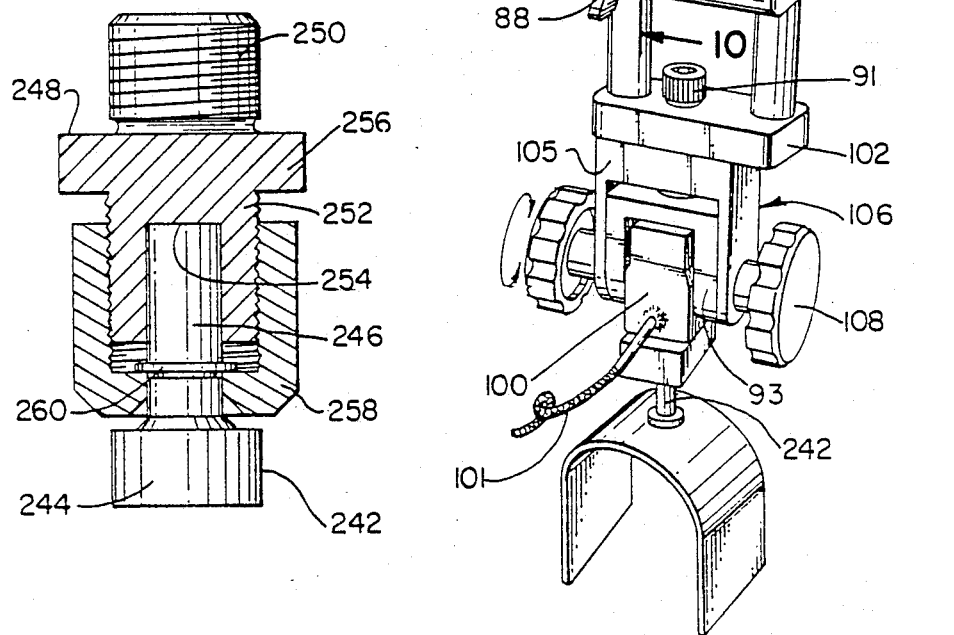
FIG. 13 is an enlarged cross-sectional view of an embodiment of an attachment apparatus for attaching the load cells to various cuffs and pads.
Figure 12:
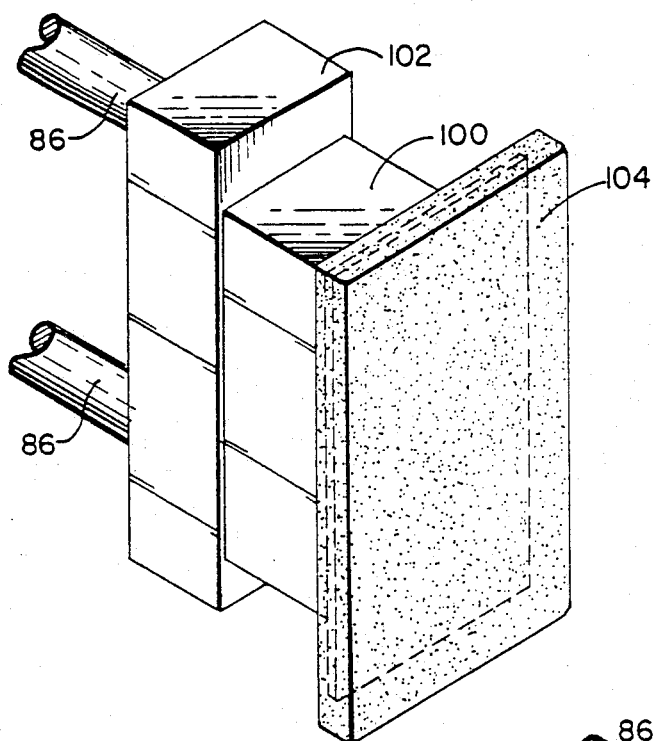
FIG. 12 is an enlarged perspective view illustrating an embodiment of a load cell mounting arrangement in accordance with the principles of the present invention.

As discussed above, positioned on the ends of the rods 86 are load cells 100. In the embodiment shown, each of the six track systems will have a load cell associated therewith. The applicant has found that in one embodiment of the present invention, signal generation and conditioning by compression/tension load cells such as 500 and 1,000 pound load cells, models SM-500 and SM-1000, as made by Interface, Inc. of Scottsdale, Arizona are particularly adaptable to the present invention. The load cells 100 when activated send an electrical signal via an electrical lead 101 which corresponds to the quantity of the force exerted by the muscle group being tested on the respective load cell 100. (This force will be exerted by the muscle group pulling (tension) or pushing (compression) on the load cell 100.) As illustrated in FIG. 12, in the embodiment shown the load cells 100 will be positioned between a rectangular member 102 similarly attached to the end of the rods 86 and a pad-like member 104 adapted for engaging that part of the body to be tested. In FIGS. 1 through 6, for purposes of illustration and clarity, the rectangular members 102 are shown without the load cells 100 attached, although as discussed above, each of the rectangular members 102 will preferably have a load cell mounted thereon. In the embodiment shown, the pad-like member 104 has a metal backing 240 and which includes an attachment apparatus for attachment to the load cells 100. In the embodiment shown, and as illustrated in FIGS. 13 and 14, the attachment apparatus includes a projection 242 which has a base portion 244 interconnected to the metal backing 240 and an elongated cylindrical projection 246. The load cells 100 in the preferred embodiment are tapped with threaded apertures at both ends. At the end of the load cell 100 interconnected to the pad-like members 104, a threaded hex member 248 is threadedly attached. When the load cell 100 is being used in a tension mode or in both tension and compression modes, the hex member includes a first threaded portion 250 for threaded attachment to the load cell 100 and a second threaded portion 252 which also includes a cylindrical aperture 254 therein. The first and second threaded portions are separated by a hex nut configuration 256 so as to enable tightening with a wrench or other suitable tools. Positioned over the cylindrical member 246 is a threaded collar member 258. A snap ring member 260 is positioned in a groove in front of the threaded collar member 258 to retain the threaded collar member on the cylindrical member 246. The pad-like member 104 is then attached to the load cell 100 by threading the threaded collar member 258 onto the threaded portion 252 of the hex member 248. In the embodiment shown, this method of attachment is slightly modified for load cells which are utilized in a compression mode only. As illustrated in FIG. 14, the hex member 248 includes a hex nut portion 252' which is not threaded. In addition, the cylindrical member 246 does not include a snap ring and the threaded locking collar 258 is not present. A rubber tube 262 is positioned over the base portion 244 and the hex nut portion 252'. In this embodiment, the base portion 244 has a slightly larger diameter than the hex nut portion 252' such that the pad-like member 104 can be attached to the load cell 100 by pushing the projection arrangement 242 against the nut member such that the rubber tube 262 is slid over the end of the hex nut portion 252' so as to frictionally engage the same. However, the pad-like member 104 can be readily removed from the load cell simply by pulling the pad-like member 104 away from the load cell. The rubber tube 262 will be retained on the projection 242 of the metal backing 240 due to the slightly larger diameter of the base portion 244. It will be appreciated that while a specific configuration for attachment of the load cells 100 to the pad-like members 104 is illustrated, any number of attachment arrangements might be utilized. Additionally, in the embodiment shown, the load cell 100 is threadedly attached to the bracket 102 by a thumb screw member 91 or the like, which might also include an alan wrench adaptor for tightening and loosening, if required.

For the testing of certain muscle groups, such as hip extension and ankle plantar flexion wherein a cuff-like attachment is used, end attachments other than a pad will be used to enable a more comfortable fit and more accurate testing of the muscle group. The cuff-like attachments might also be padded with a pad-like material 264 for the subject's comfort. In addition, in order to assure proper alignment with the muscle group being tested, a pivotal mounting assembly for the load cell 100 might be required. Illustrated in FIG. 9 is a pivotal mounting assembly 106 which includes a U-shaped bracket 105 threaded onto the bracket 102 and secured by the threaded member 91. Pivotally mounted inside the first U-shaped bracket is a second U-shaped bracket 93 and knobs 108 are used to tighten and loosen the U-shaped bracket 93 as required such that the U-shaped bracket 93 may be pivoted about an axis extending between the knobs 108 to any desired location and then tightened in place. Suitably secured to the U-shaped bracket 93 is the load cell 100 and its corresponding electrical lead 101. This type of pivotal mounting assembly is particularly useful when testing knee extension/flexion, wherein the load cell 100 is aligned with the ankle at an angle which is neither horizontal nor vertical. Accordingly, the pivotal mounting assembly 106 enables the load cells of the present invention to be properly aligned with the muscle group being testing regardless of the angle of alignment.

Illustrated in FIGS. 15 through 19 are various cuff-like assemblies which are used for testing various muscle groups. Illustrated in FIG. 15 is a thigh cuff 99 which has a greater radius of curvature than front and back leg cuffs 97, 98 shown in FIG. 19, as the thigh cuff 99 is adapted to be positioned over the thigh when doing ankle plantar flexion testing. Illustrated in FIGS. 16 and 17 are right and left ankle cuffs 94, 95 which are positioned over the ankle during ankle dorsiflexion testing. Illustrated in FIG. 18 are upper and lower knee cuffs 107, 109 which are shown threaded together by a restraining strap 111. The upper and lower knee cuffs 107, 109 are positioned on top of and under the leg, respectively, just behind the knee when measuring hip extension. When measuring hip flexion, only the upper knee cuff 107 is utilized. Illustrated in FIG. 17 are the front and back leg cuffs 97, 98 which are merely strapped to the lower leg when performing knee flexion testing and which are interconnected by a Velcro strap 96. When performing knee extension testing the back leg cuff 98 is removed.

As illustrated in FIG. 9 and FIGS. 15 through 19, the cuff attachments are attached to the load cells 100 by the projection 242 in a manner as described above for the pad-like members 104.

Figure 20:
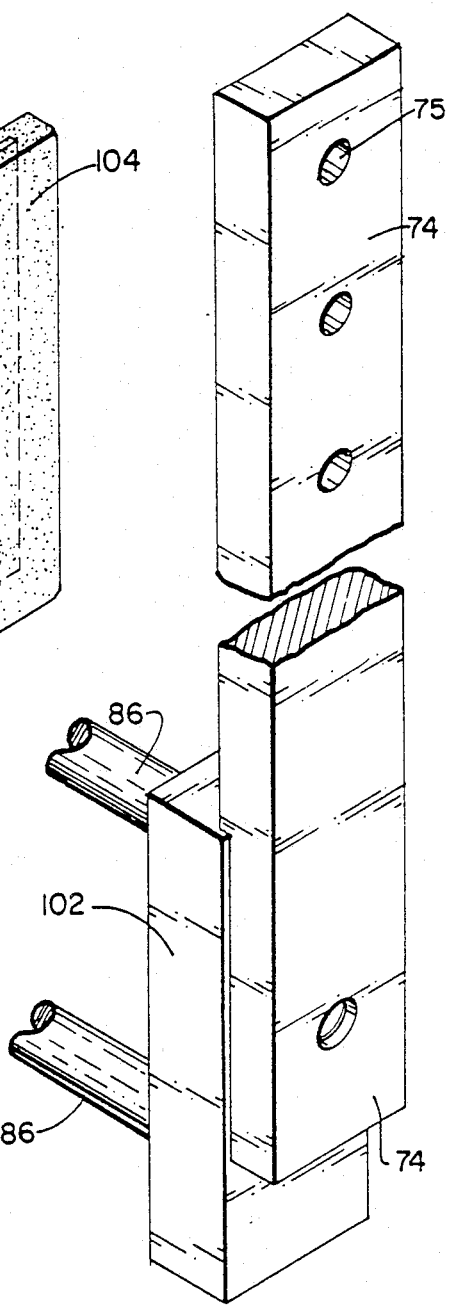
FIG. 20 is an enlarged fragmentary perspective view of an embodiment of an extension apparatus in accordance with the principles of the present invention.

As illustrated in FIG. 20, in certain embodiments of the present invention it might be necessary to attach a vertical extension onto the rectangular members 102 to assure sufficient height for testing of the neck muscles in the case where the track system is not high enough to enable such testing. For example, an elongated rectangular member 74 having a plurality of threaded apertures 75 therein might be threaded onto the rectangular members 102 and the load cells 100 and their associated pad-like members 104 threadedly attached to one of the apertures 75 of the rectangular members 74. In particular, such vertical extension members might be utilized on the posterior track 80a, the left and right lateral tracks 80b,c and the anterior track 80d when testing of the neck muscle group occurs. The vertical extension apparatus will preferably be removably attached so as to not interfere with the other muscle testing.

As discussed earlier, the load cells 100 must be properly aligned and positioned with respect to the muscle-joint being tested. The track system of the present invention makes this possible for a plurality of muscle groups. The pivotal mounting assemblies 106 further extend the capability to properly align the load cell sensors with the various muscle groups.

Figure 21:
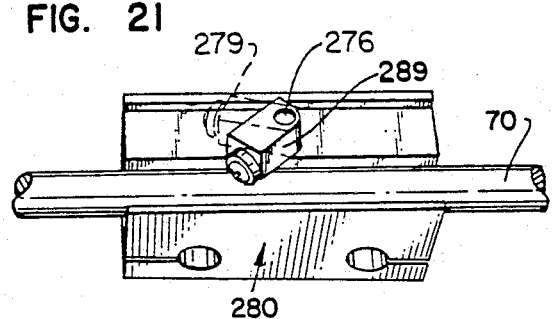
FIG. 21 is a perspective view of an embodiment of a latch mechanism.
Figure 22:
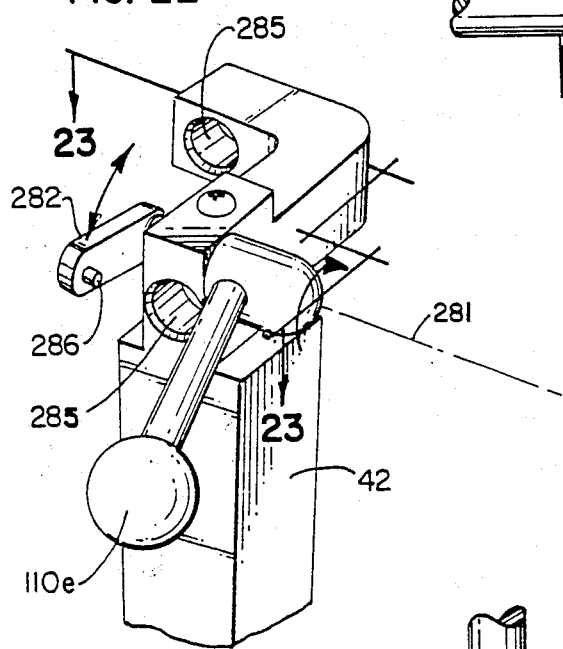
FIG. 22 is a perspective view of yet another embodiment of a latch apparatus in accordance with the present invention.
Figure 23:
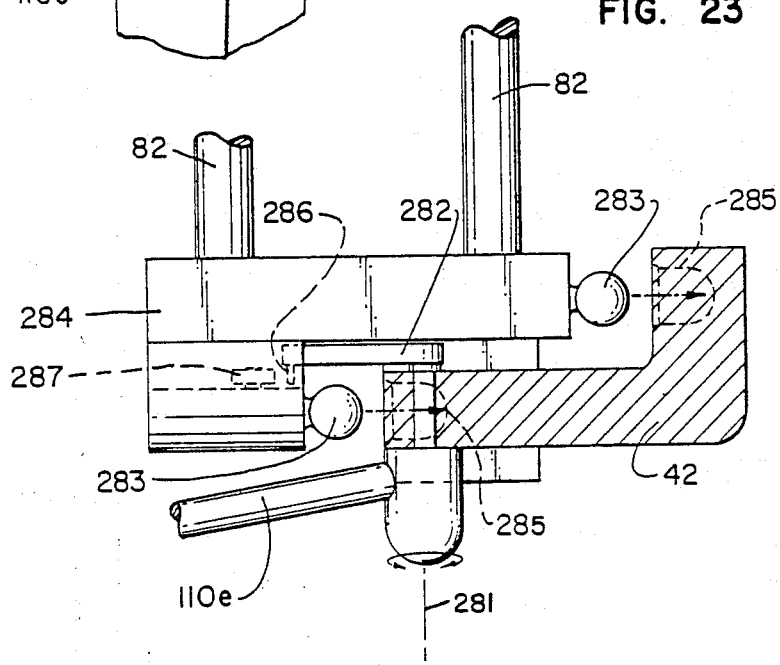
FIG. 23 is a view as seen generally along line 23 in FIG. 22.

The anterior track 80d, the forward upper track 80e, and the forward lower track 80f each include latch mechanisms 110d,e,f, respectively, which enable those tracks to be pivoted away from in front of the chair apparatus 40 such that the subject can gain access to and readily be seated in the chair apparatus 40. When the latch mechanisms 110d,e,f are unlatched, their respective tracks 80d,e,f are capable of pivotal movement about a vertical axis as illustrated by arrows 112d,e,f in FIG. 2. (In the Figures, numerous arrows are present to illustrate some of the possible movement of the various parts.) Illustrated in FIG. 21 is an embodiment of a latch for the anterior track 80d and the lower forward track 80f. The latch includes a pivotal member 289 which is pivoted about an axis 276 so as to latch the mounting attachment 280 onto the cylindrical rod member 70 of the support frame 42. The latch is shown in its released position by phantom line 279. Illustrated in FIGS. 22 and 23 is a ball and socket latch for the upper forward track 80e which includes a member 282 which pivots into and out of a locked position about an axis 281. Once ball members 283 on an end portion 284 have been inserted into their respective sockets 285 in the support frame 42, the latch 110e is pivoted upward such that a projection 286 on the member 282 pivots about the surface of a cylindrical bearing 287 into an over center position so as to firmly nudge the latch into the secured or latched position and retain the track system 80e in place. In the latched position, the projection 286 will be positioned along an arc of the bearing 287 so as to retain the bearing 287 in position.

As previously discussed, the present invention is capable of immobilizing or stabilizing muscle groups of the various body parts which would normally have a tendency to assist the muscle group being tested and thus interfere with accurate test readings, unless so immobilized. In the embodiment of the chair apparatus 40 as illustrated in FIGS. 1 through 6, a thorax or upper chest restraint assembly 120 is provided. As illustrated in FIG. 7, the thorax restraint assembly 120 includes a rectangular pad 122 which is slidably mounted on the rods 82 of the posterior track 80a by an arrangement somewhat similar to that previously described for the load cells. In particular, the slidable arrangement includes a block member 124 and a latch 126 enabling adjustable positioning along the rods 82 of the posterior track 80a. Block member 124 includes a bore adapted for receipt of a cylindrical rod 128 extending generally perpendicularly of the posterior track 80a with a latch 130 enabling slidable positioning of the cylindrical rod 128 in the block 124. The rectangular pad 122 is pivotally attached to the end of the cylindrical rod 128 for pivotal motion about a horizontal axis with a latch 132 being provided to secure the pad 122 in position. The rectangular pad 122 includes apertures along the sides of its metal backing 123 adapted for receipt of a webbed belt 134 which can be positioned about the thorax or chest of the subject and snugly fastened by use of a conventional buckle assembly or the like. Accordingly, this enables the subject's thorax or upper chest to be immobilized or fixed against movement.

Additionally, slidably mounted on the posterior track 80a at a position below the thorax restraint assembly 120 is a sacral pad assembly 140. As with the thorax restraint assembly 120, the sacral pad assembly includes a pad 142 mounted on the end of a cylindrical rod 144 which is slidably mounted in a block member 146. As discussed above, the block member 146 can include a latch or lock (not shown) to fix the position of the rod 144 and/or enable horizontal adjustment thereof. Additionally, the block member 146 includes a latch or lock (not shown) which enables the sacral pad assembly 140 to be adjusted vertically. Furthermore, the sacral pad 142 is pivotally mounted on the end of the rod 144 at 143 to enable tilting and/or twisting of the pad to fit comfortably against the lower portion or sacral of the subject's back. Accordingly, the sacral pad assembly provides for sacral restraint.

A pelvic restraint assembly 150 includes a four inch webbed strap 152 which is attached at one end to a base portion of the seat assembly 46 along the left side of the seat assembly 46 toward the back of the seat pad 50. The other end of the four inch webbed strap 152 is interconnected to the other side of the seat assembly 46 by a conventional seat buckle arrangement.

When the subject is seated all the way back on the seat pad 50 so that the back of the lower legs are against the front of the seat pad 50, a thigh restraint strap 160 attached at one end to the side of the seat assembly 46 is placed over the subject's left leg and then down between the subject's legs through two slots 162 formed in the base of the seat assembly, and then over the right leg. The thigh restraint strap 160 is then attached to the other side of the chair assembly 160 by a conventional seat buckle arrangement such that the thigh restraint strap can be adjusted to fit the subject snugly and properly restrain the thighs.

A calf restraint assembly 170 is also provided for restraint of the calf portions of the subject's leg. The calf restraint assembly 170 includes two cur vilinear pads 172 mounted on a metal backing 171 which are adjustably mounted for vertical movement. In addition, calf pads 172 are pivotally mounted to enable tilting of the pads upwardly and downwardly and twisting of the pads from side to side. The calf pads 172 include restraining straps 176 which are wrapped around the front of the subject's lower legs and through threaded slots in the calf pads 172. The end of the restraining straps 176 might be suitably fastened by the use of Velcro fasteners, etc. In use, after the patient or subject is properly seated and the plates 66 are adjusted to the proper height and position, calf pads 172 are adjusted to approximately six inches above the platform 64 by the use of lock knobs 178. The calf pads 172 are then pivotally maneuvered into a comfortable position and locked in place with levers 174. Calf restraint straps 176 are then wrapped around the front of the lower legs and suitably fastened so as to effectively restrain the calves as required.

Figure 4:
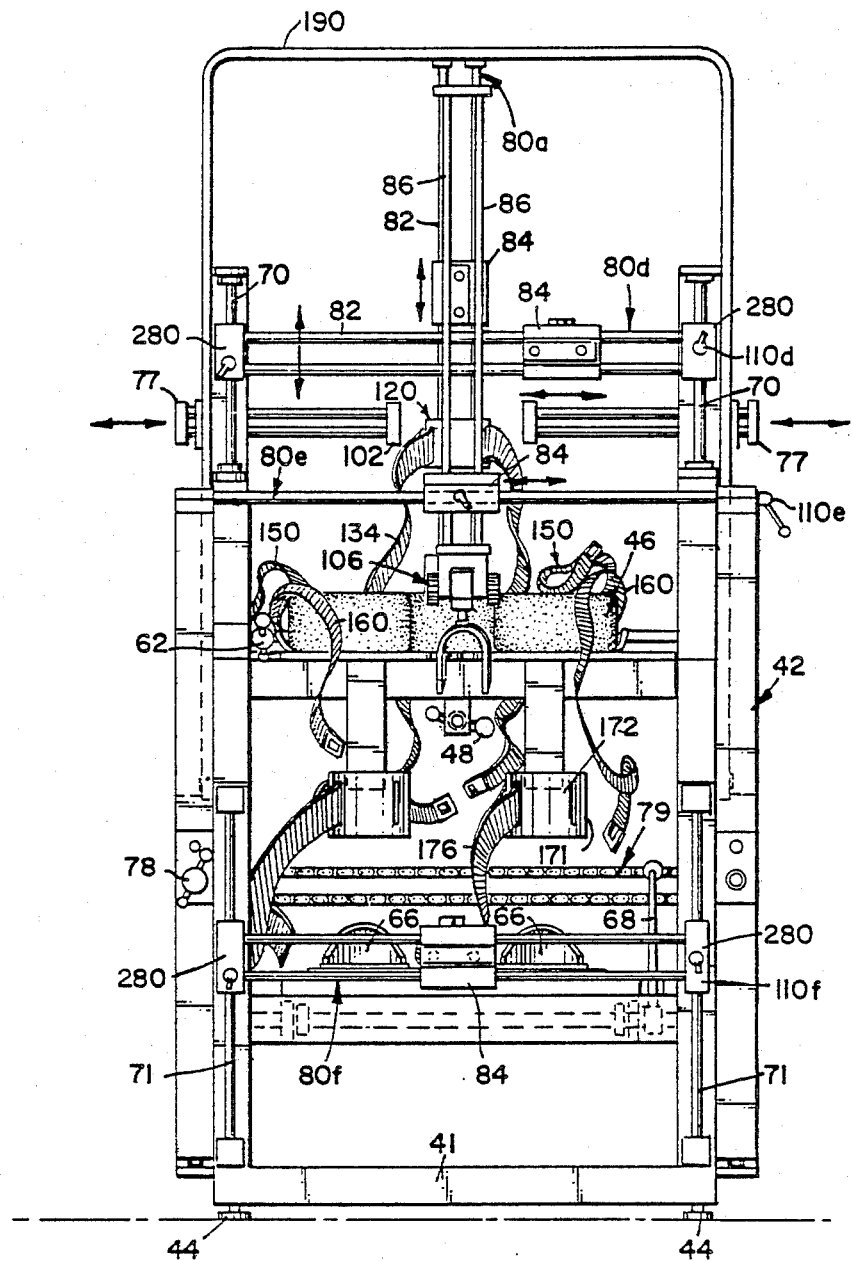
FIG. 4 is a view of the embodiment shown in FIG. 1, as seen generally from the front.
Figure 5:
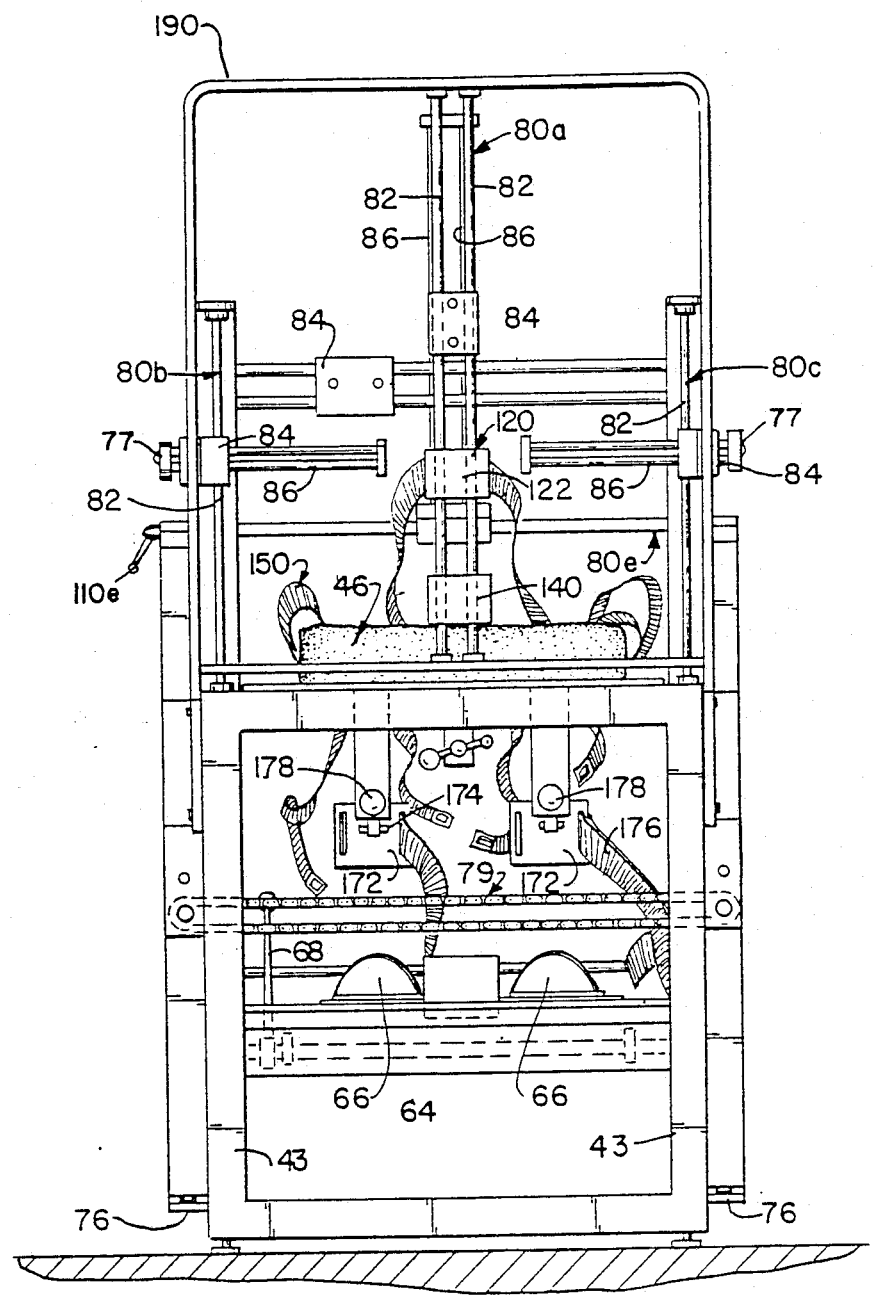
FIG. 5 is a view of the embodiment shown in FIG. 1, as seen generally from the back.
Figure 6:
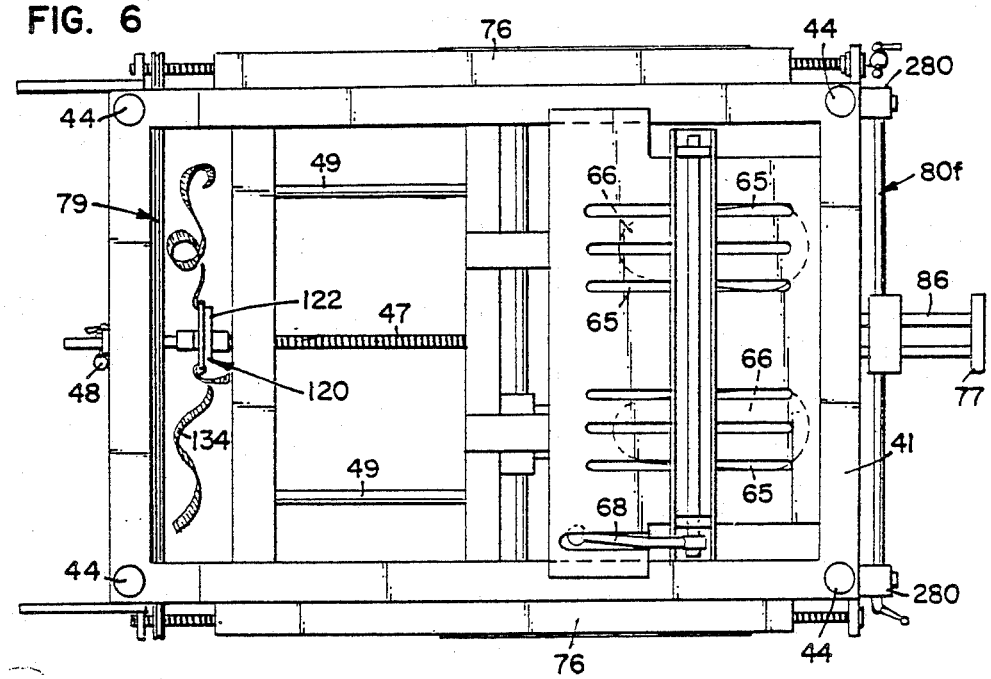
FIG. 6 is a view of the embodiment shown in FIG. 1, as seen generally from the bottom.

Illustrated in FIG. 4 is an alternate embodiment wherein calf restraint assemblies are interconnected to the foot plates 66, as opposed to the seat assembly 46. As with the previous calf restraint assemblies, each of the calf restraint assemblies 266 includes a curvilinear pad 268 mounted on a metal backing 270. The pads are in turn pivotally mounted by a pivotal mounting mechanism 272 as illustrated by the arrows in FIG. 4. In addition, the restraining straps 274 are interconnected to the metal backing 270. As illustrated, the calf restraints 266 are mounted for vertical movement in a pedestal 271 secured to the foot plates 66, a hand held knob 273 being used to secure the calf restraints at the proper vertical height.

Figure 24:
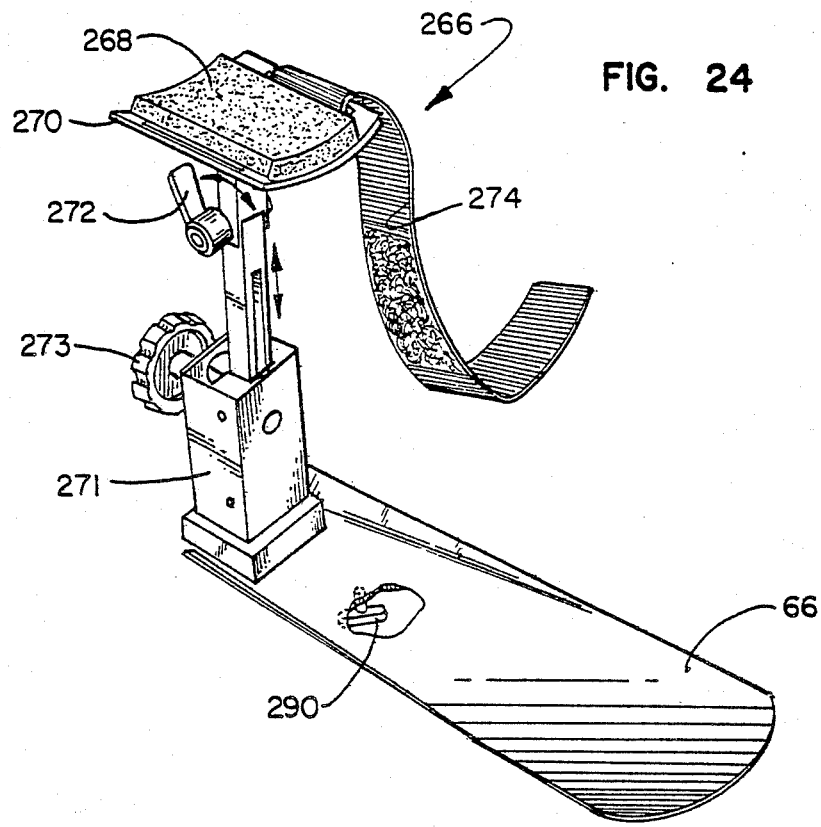
FIG. 24 is an enlarged perspective view of an alternate embodiment of the foot plates and calf restraints in accordance with the principles of the present invention.
Figure 25:
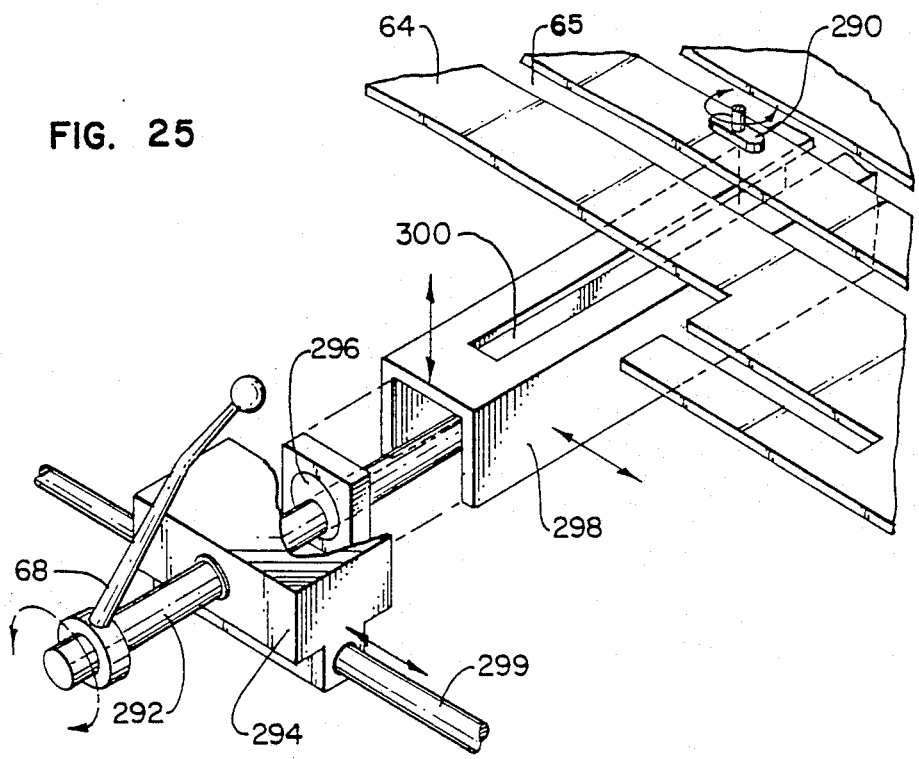
FIG. 25 is a perspective view of an embodiment of the mechanism for securedly attaching the foot plates to the foot rest assembly.

As previously discussed, the foot plates 66 are positioned in slots 65 of the foot rest platform 64. As illustrated in FIGS. 24 and 25, the foot plates include a T-shaped member 290 attached to a bottom surface thereof. The T-shaped member 290 is narrow enough to be inserted through the slots 65 but has a length greater than that of the slots 65, so when twisted into position the T-shaped member 290 prohibits the foot plates from being removed from the platform 64. As illustrated in FIG. 25, the lever 68 is interconnected to a cylindrical rod 292 suitably mounted in pillow block assemblies 294. Moreover, mounted for rotation with the rod 292 are eccentric cam members 296. The rod 292 and its associated cam members 296 support a U-shaped rectangular member 298 which has slots 300 in a top surface thereof adapted for receipt of the T-shaped member 290. By moving the lever 68 upwardly or downwardly, the U-shaped rectangular member 298 is caused to move vertically. Accordingly, the foot plates 66 are fixedly secured to the platform 64 by pushing down on the lever 68 such that the U-shaped rectangular member 298 engages the T-shaped member 290 and pulls down on the foot plates 66. The foot plates 66 are then loosened by pulling up on the lever 68 such that the U-shaped rectangular member 298 is forced upward towards the platform 64, thereby releasing the T-shaped member 290. Accordingly, the foot plate 66 can then be adjusted as required by twisting the foot plates or they can be removed by properly aligning the T-shaped member 290 with the slots 65 in the platform 64 and the U-shaped rectangular member 298. Moreover, as illustrated, the lever 68 is slidably mounted on supportes 299 for forward and backward adjustment of the foot plates 66 which aid in stabilizing a subject's feet.

As previously discussed, the foot rest assembly 60 can be adjusted vertically to serve as a foot restraint. This is accomplished by use of a chain and screw rod assembly wherein by turning the crank 62 a continuous chain contained in the framework along bottom frame portions 41 causes the screw rod members 61 in frame uprights 43 to turn whereby the foot rest assembly 60 is raised or lowered. It will be appreciated that any number of apparatus might be utilized for this purpose.

Figure 3:
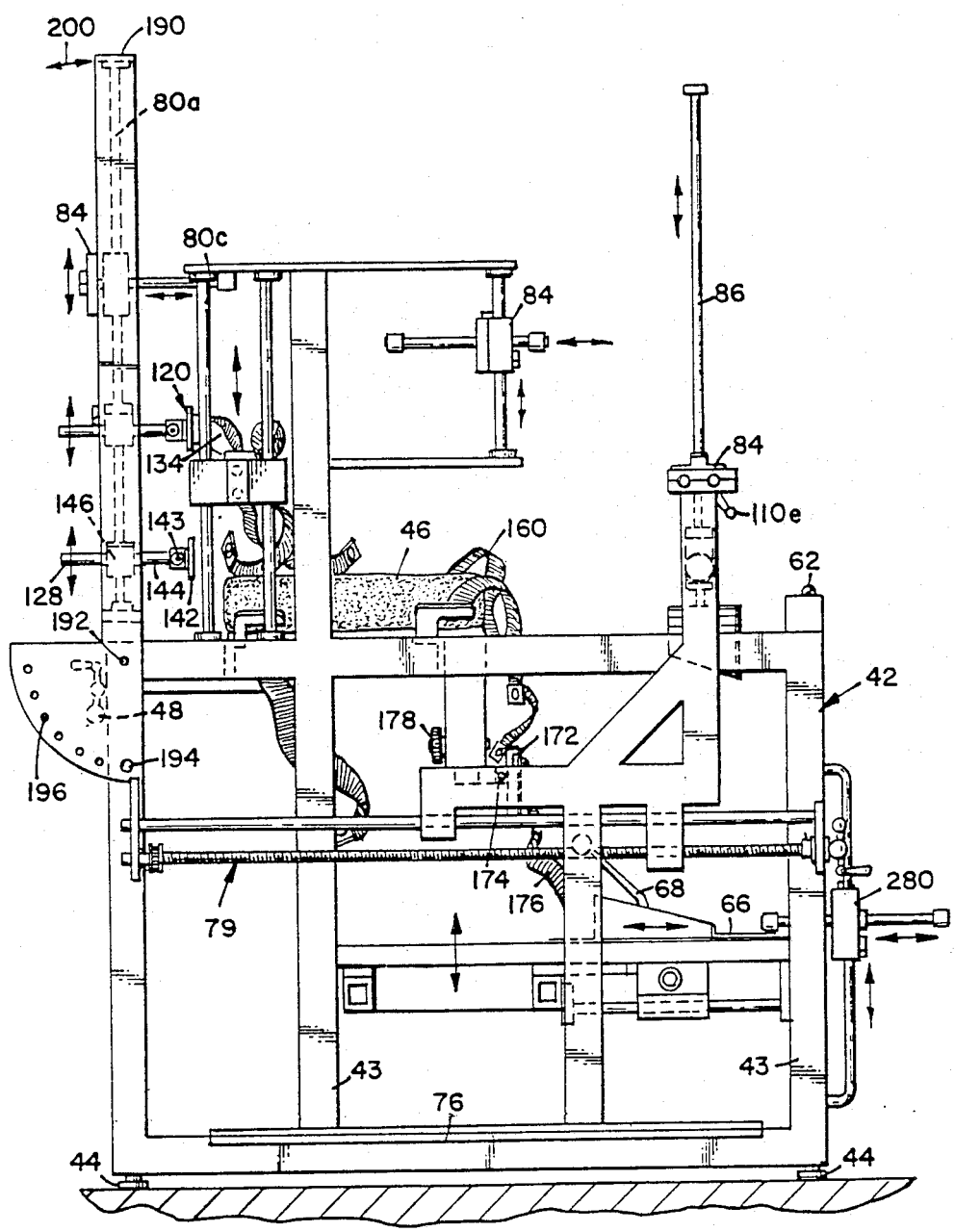
FIG. 3 is a view of the embodiment shown in FIG. 1, as seen generally from the side.

A back frame portion 190 of the support frame structure 42 supports the posterior track 80a and is pivotal about a horizontal axis at 192 such that the back frame portion 190 can be oriented at various angles of inclination during the testing process. As illustrated in FIG. 3, the back frame portion 190 is maintained in its position by a lock pin 194 inserted through any of a plurality of apertures 196 arranged in an arc and into a frame member 198. As illustrated by an arrow 200, this enables the back frame portion 190 to be oriented at a number of different orientations.

Figure 30:
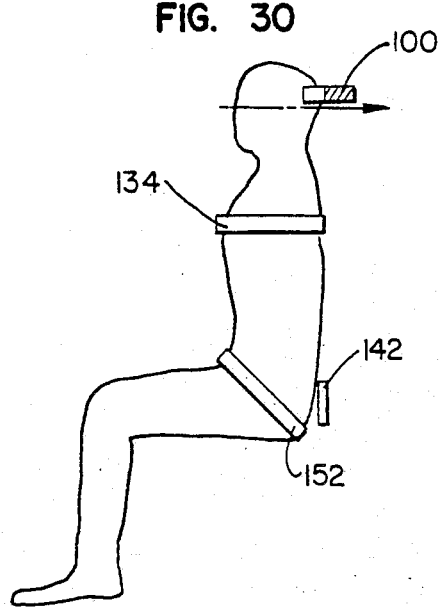
Figure 31:
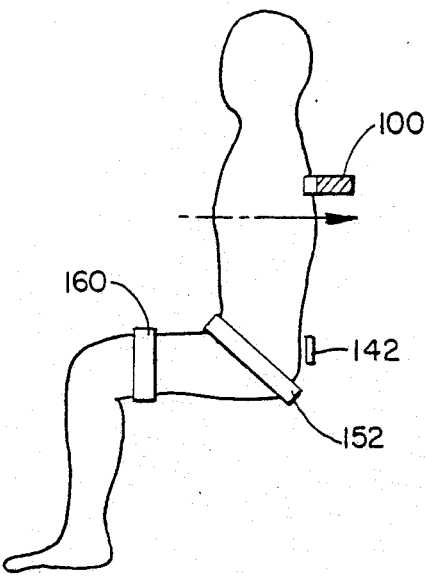
Figure 32:
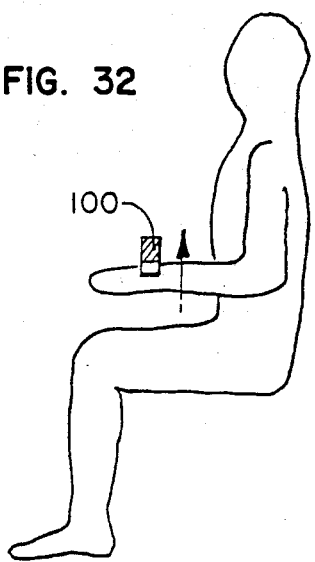
Figure 33:
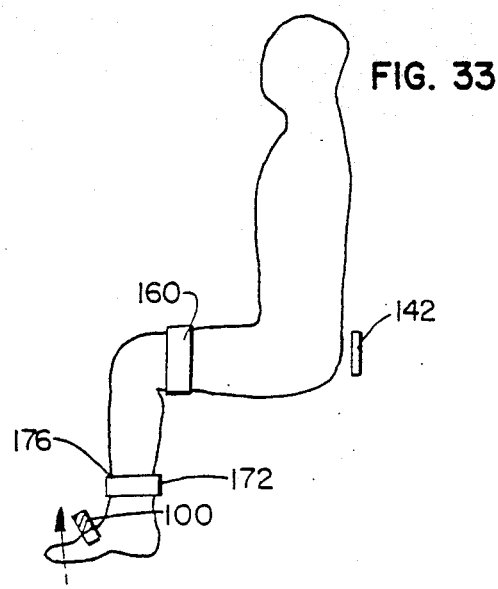

Illustrated in FIGS. 26 through 33 are diagrammatic views generally illustrating positioning and immobilization of the subject and of the load cells 100 relative to the muscle group being tested for the following muscle groups:

| | |
|---|---|
| FIG. 26 | Hip flexion |
| FIG. 27 | Hip extension |
| FIG. 28 | Knee extension/flexion |
| FIG. 29 | Ankle plantar flexion |
| FIG. 30 | Neck extension |
| FIG. 31 | Trunk extension |
| FIG. 32 | Elbow flexion |
| FIG. 33 | Ankle dorsiflexion |

It will be appreciated that these Figures are intended to be diagrammatic only and are meant as an aid in understanding relative positioning of the various immobilization devices and load cells when testing various muscle groups. Throughout this specification the term "flexion" is generally used to indicate contraction of the muscles which reduce the angle of two or more bones which constitute a joint, whereas "extension" is generally used to indicate contraction of muscles which increase the angle between two or more bones which constitute a joint.

Use of the chair apparatus 40 will now be described in terms of testing hip flexion/extension. It will be appreciated that use of the chair apparatus 40 for testing other muscle groups would require immobilization of the subject and positioning of the load cells for the specific muscle group being testing. To test hip flexion/extension, the subject is seated in the chair apparatus 40 and the pelvis is immobilized by use of the pelvis restraint assembly 150. The four inch strap 152 is secured and adjusted so as to be comfortable yet fit firmly over the pelvic area of the subject. The anterior track 80d is unlatched with the latching mechanism 110d on the left side thereof and swung open and out of the way to allow the upper forward track 80e to be moved backward toward the subject by use of the crank 78. Prior to moving the upper forward track 80e, the load cell mounted thereon is raised to a vertical height above the subject's thigh. The load cell mounted on the upper forward track 80e is moved backward toward the subject until it is in a position approximately four inches in back of the subject's knee. When properly positioned above the subject's thigh/knee, the load cell 100 and its associated knee cuff are placed over the leg. The cuff is firmly placed on top of the leg and locked in place. The seat assembly 46 should be moved backwardly to the rear as far as possible using the crank 48 so that the thigh extends over the front of the seat pad 50. The sacral pad should be adjusted to a comfortable position and locked into place. The pelvis and thorax should be secured or immobilized using the pelvic restraint assembly 150 and the thorax restraint assembly 120. The foot rest assembly 60 is lowered to a position approximately one inch below the extended foot so that the foot is not forcing against the foot plate assembly 60. Although not shown, shoulder restraint straps might be used to secure the upper trunk. The user then exerts force in a direction generally upward by raising his/her leg as generally illustrated in FIG. 26. To measure hip extension, the upper and lower knee cuffs 107, 109 are positioned just behind the knee and threaded together by use of the restraining strap 111. The upper knee cuff 107 is then threaded onto the load cell 100 and the subject pushes his/her thigh generally downwardly as illustrated in FIG. 27.

It will be appreciated that additional muscle strength testing devices such as handgrip and pinch devices might be attached to the chair apparatus 40 to enable testing of additional muscle groups.

Figure 34:
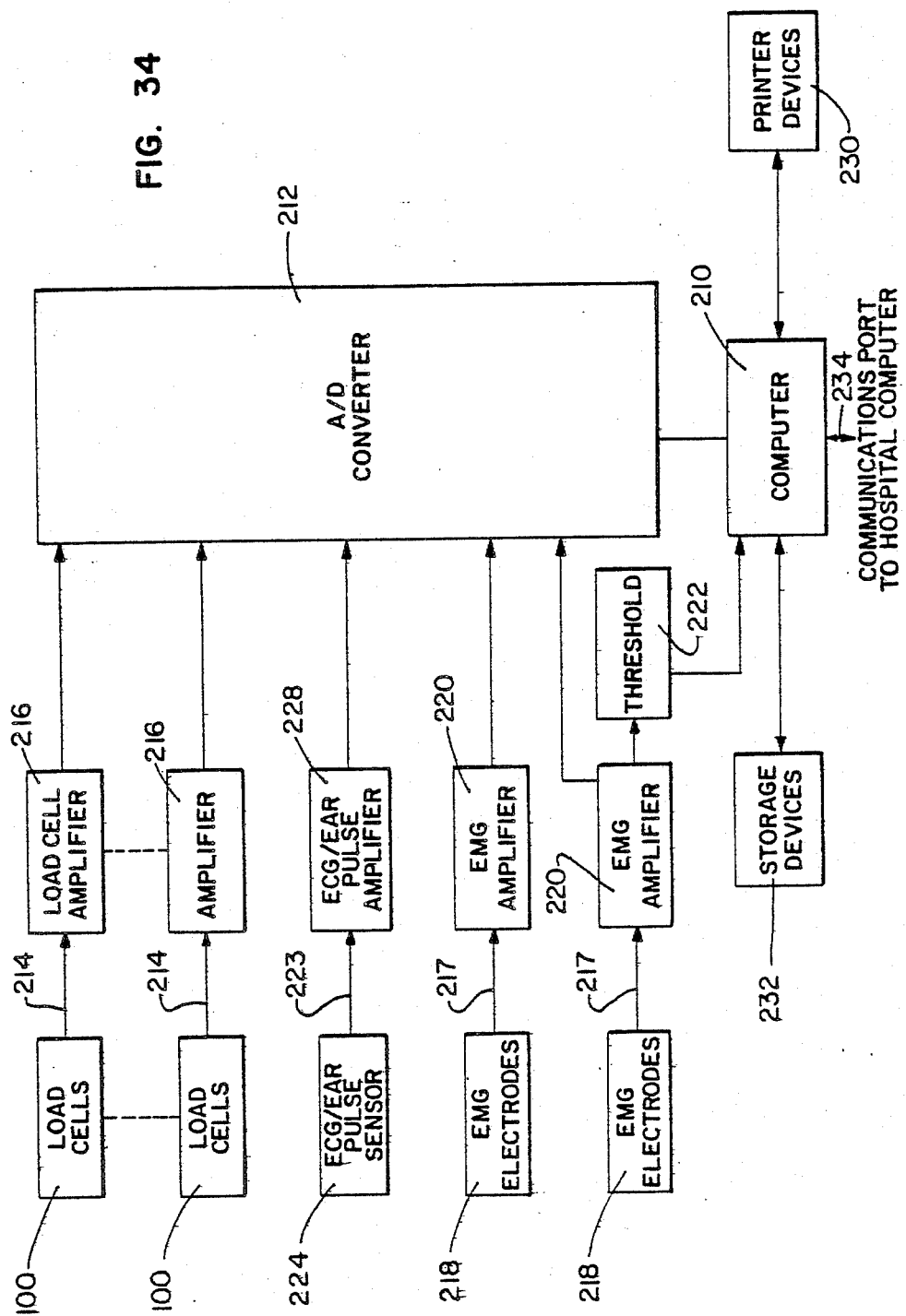
FIG. 34 is a block diagram of a computer controlled system in accordance with the principles of the present invention.
Figure 37:
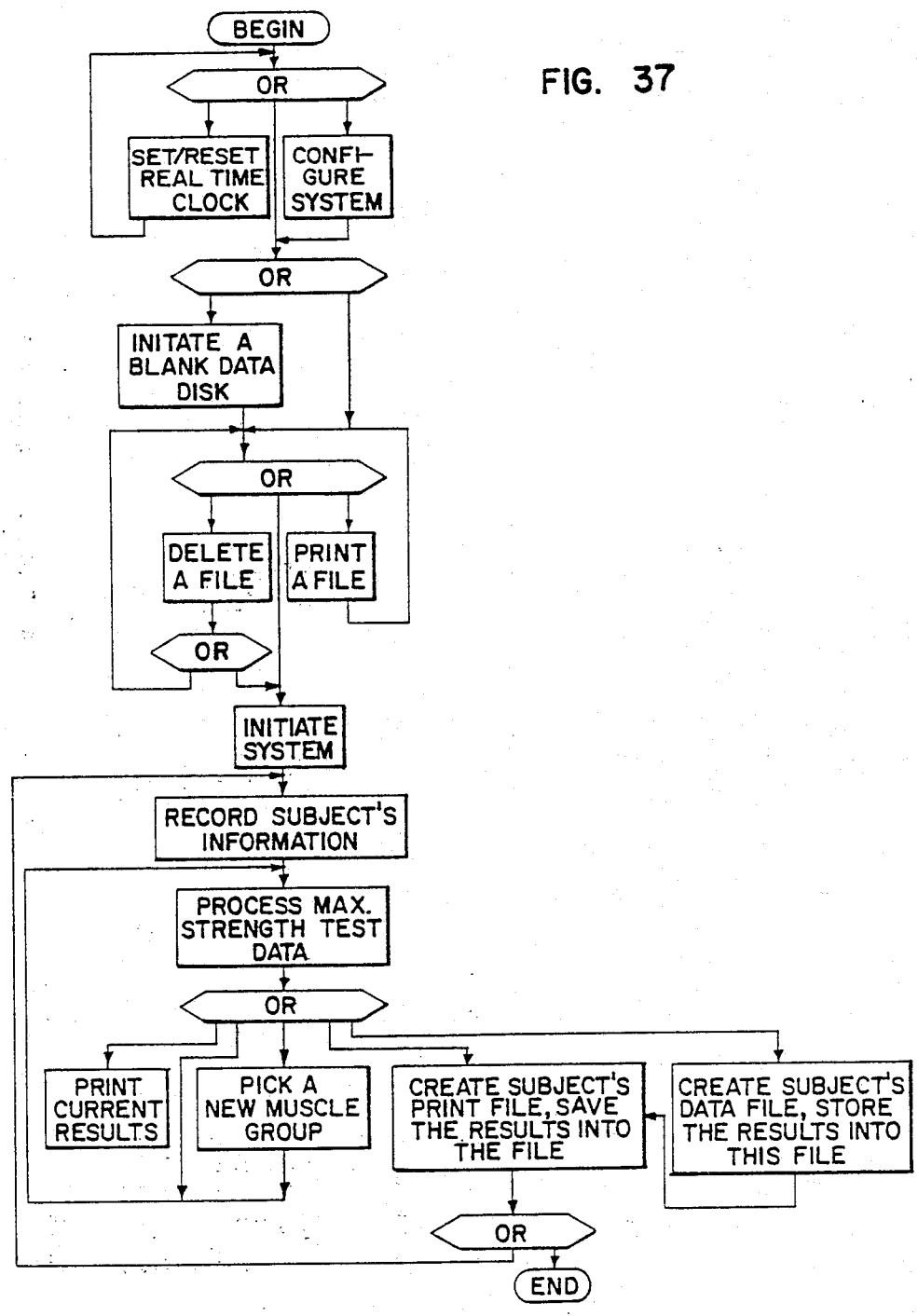
FIG. 37 is a logic flow diagram of an embodiment of a logic sequence implemented in accordance with the principles of the present invention.
Figure 38A:
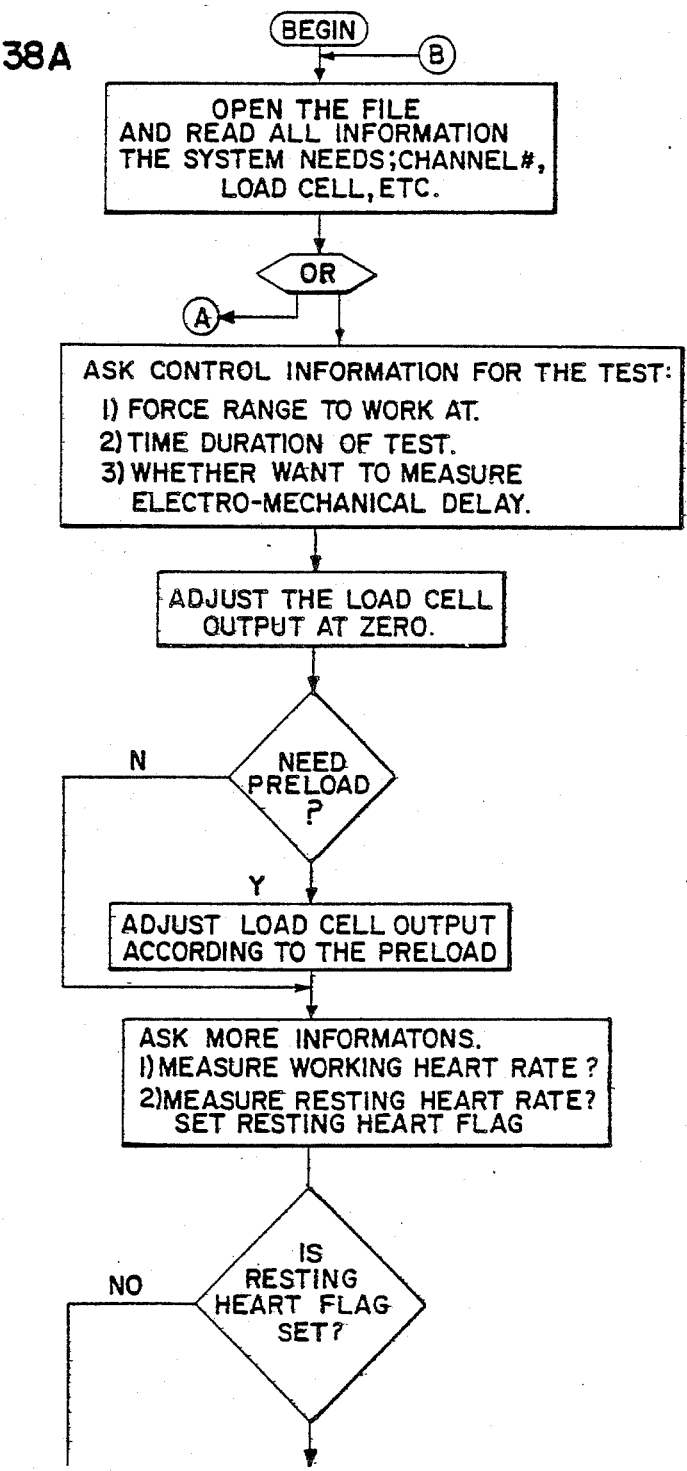
FIGS. 38A–C are logic flow diagrams of an embodiment of a logic flow sequence for processing various input parameters.
Figure 38B:
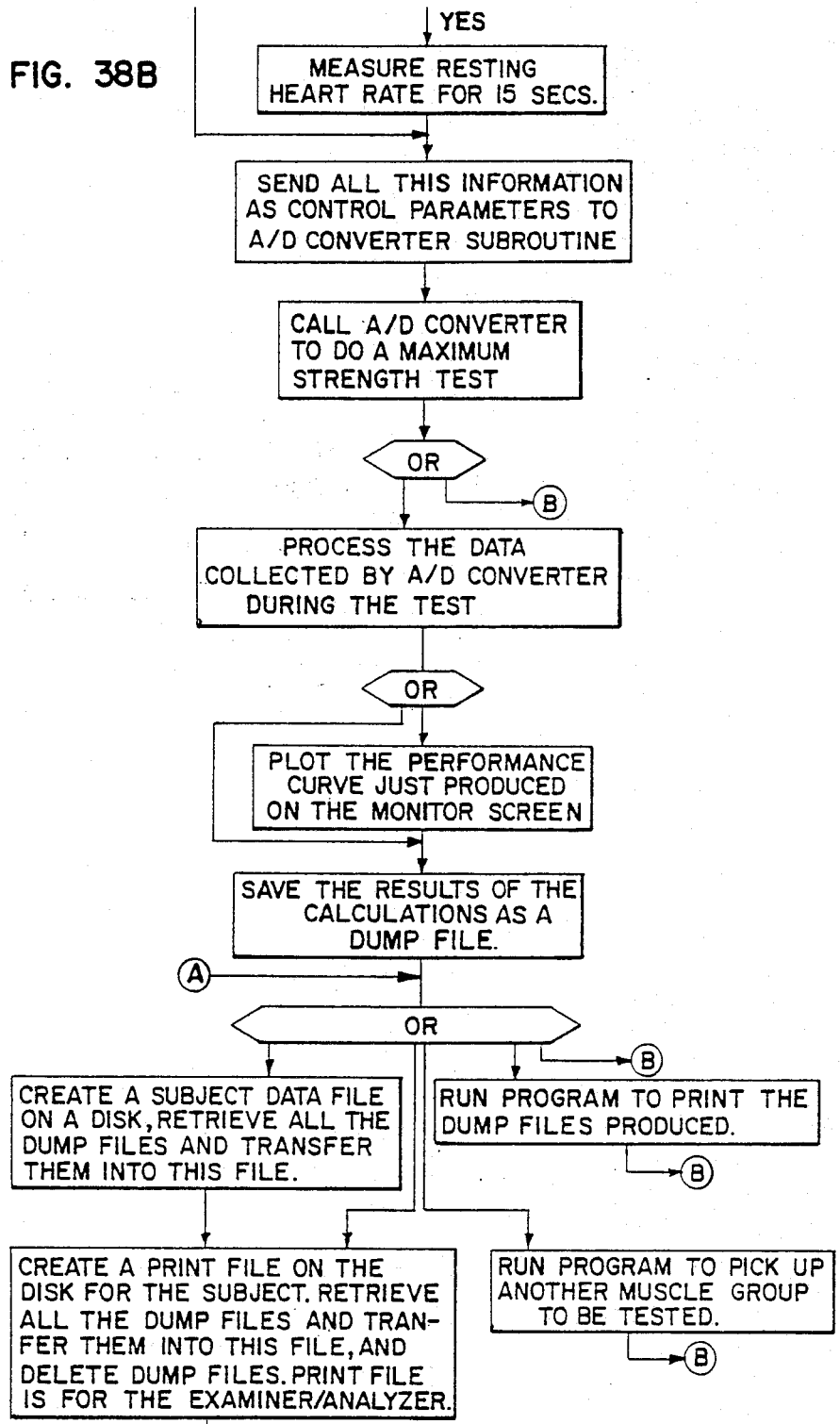
Figure 38C:
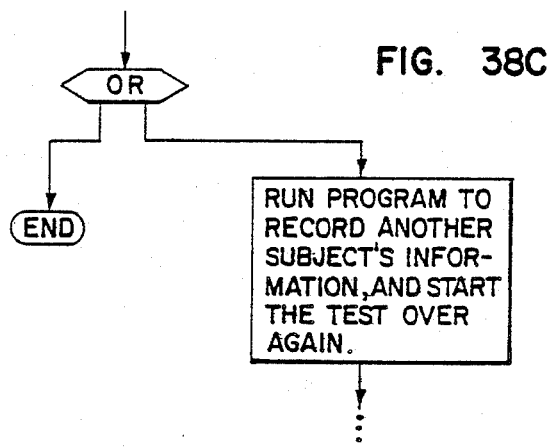

As illustrated in FIG. 34, one embodiment of the present invention includes a computer controlled system which includes a microcomputer 210, such as an Apple IIE with 128K of RAM memory, a 12 bit, 16 channel analog to digital converter 212 which is interconnected to the microcomputer 210, eight load cell channels 214 and associated gain and offset controls and analog filters 216 which are connected to the analog to digital converter 212, two channels 217 for electromyographic amplifiers (EMG) 218 and their associated gain controls and filters 220 which are interconnected to the analog to digital converter 212. One of the EMG channels has a threshold detector circuitry 222 which is used to provide a digital output at the start of a muscle contraction to indicate the beginning of electrical activity in the muscle. In addition, there is an ear pulse sensor 224 or ECG electrodes which input through a heart rate channel 223 and associated gain controls and analog filter circuitry 228 for output of a digital pulse for each heartbeat. The computer 210 is programmed to provide signal processing of the data collected, printing of results from a printer device 230, storage of the data on a storage device 232 and/or transfer of data to a main central computer and/or client data base via a communications line 234.

In one embodiment of the present invention, the computer programs consist of three main programs:
(1) maximum strength testing;
(2) muscle endurance testing; and
(3) muscle exercise control.

The first two programs allow the user to input patient characteristics (i.e., height, weight, etc.) and then select a muscle group for testing from a list of 24 muscle groups. The selection of the desired muscle group automatically activates the needed load cell 100 from the eight which are potentially available. As previously discussed, the embodiment of the chair apparatus 40 illustrated in FIG. 1 will typically make use of six load cells, one for each track system.

The first program deals with muscle strength testing. In one embodiment of the program, up to six repeated measurements of up to six seconds in duration can be made with up to six seconds of rest in between. During this test program, the slope of the decay of the force with each contraction is not calculated as the purpose of this test is to make rapid measurements in order to profile the body strength in a minimum time using only one or two testing periods. This program allows for rapid testing of the various muscle groups and is often referred to as a quick test. It will be appreciated that the time intervals can be varied as preferred.

In both the strength testing and the endurance testing, the patient's or subject's action is directed by a tone generated by the computer which signals the patient or subject to take some action.

A plurality of parameters, illustrated in FIG. 35, are measured during the maximum force test and are defined as follows:

(1) The delay time ($T_d$) is the time from the starting tone to the point where the force curve rises to 10% of peak force value.

(2) The rise time ($T_r$) is the time the force rises from 10% of the peak force to 90% of the peak force value.

(3) Electromechanical delay (EMD) is the time from the start of the EMG to the point where the force rises to 10% of the peak force value.

(4) Peak force ($F_p$) is the maximum force occurring during the measurement period.

(5) The end force ($F_e$) is the average force occurring during the last one second of the measurement period.

(6) The average force ($F_a$) is the average force over the entire measurement period.

(7) The linear slope of the force decay is measured from 800 milliseconds after $T_d$ to the end of the muscle contraction.

The endurance testing makes measurements at a submaximal force level for continuous contractions or periodic work/rest cycles. The subject is shown a line on the screen which represents a percentage of his/her maximum strength. The subject is instructed to produce a contraction which moves a dot up to the line each time a tone is heard. Stopping conditions can be either a fall in the force to a given level or a chosen time of duration. The force parameters measured are as follows:

(1) The average force over the entire run;
(2) The duration of the run;
(3) The slope of the decay of the average force as a function of time;
(4) Data on individual contractions
 (a) Peak force ($F_{pm}$).
 (b) Average force during the tone signal ($F_{am}$).
 (c) Maximum force ($F_{dm}$) averaged over the length of time of the signal tone as a function of delay of from forty to four hundred milliseconds. This attempts to account for the delay in starting and stopping of the contraction.
 (d) The delay time ($T_{dm}$), at which $F_{dm}$ occurs in part (c) above.
 (e) The electromechanical delay (EMD).

(5) The EMG is sampled up to ten times with 0.5 second periods during the measurement period and stored for later analysis.

The exercise control program was developed to allow the system to be used for isometric exercise training. This program allows the user to select various work levels expressed as a percentage of the user's maximum strength. The user will then exercise for a given number of repetitions at one level and then be increased to a higher level. The number of repetitions completed at each level of work is saved for a further review.

The programs were designed to be user friendly and menu driven. Illustrated in FIG. 36 is a sample printout obtained after three periods of testing. General logic flows for the programs is shown in FIG. 37 and FIGS. 38A-C. They provide for entry of patient descriptive data that is automatically attached to the quantitative data derived from the test. The system typically requires two disk drives. One is used for the programs and the other for storage of data. When the system disk is loaded all of the parameters and programs that are used are read into the extended 64K memory which serves as an electronic disk and appears to the operating system as another disk drive. This enables for a very fast exchange of programs and storage of data. After the system has been loaded, the display shows the patients' records that are saved by name, date, time and the amount of space remaining on the disk in terms of the number of additional tests that could be saved. At this point the user can either print out existing data and/or delete records. The user is then asked for patient descriptive data such as name, age, weight, etc. The user next chooses disease descriptors from a major category selection of twenty one types and then further describes the disease from a subcategory list which has a total of 158 entries. The selection of the muscle to be tested is done next, which also automatically selects the correct load cell for the measurement.

Next, a series of menus appear which relate to the parameters of the test. For the maximum strength test, the following parameters can be selected:
(1) maximum force range;
(2) duration of the test; 2.5, 5 or 10 seconds;
(3) measurement of the electromechanical delay;
(4) the use of a preload on the muscle. If chosen, the computer will measure the changes from the preload value and record the value of the preload.

For the endurance test, the following parameters can be selected:
(1) desired working strength level expressed as a percentage of the maximum strength;
(2) stopping conditions (time or force level);
(3) measurement of electromechanical delay;
(4) measurement of EMG data for frequency analysis.

After the user selects the desired option, a graph is shown which displays time and amplitude axes. Upon depressing "return" a tone is sounded which directs the patient to contract the desired muscle.

The computer controlled embodiment of the present invention will allow clinicians to obtain quantitative profiles of the isometric muscle strength in a plurality of muscle groups in the human body. Most equipment currently available focuses on the knees or only a few other muscle groups Besides providing a very understandable parameter, like maximum muscle strength, the present invention also provides a number of measurements related to the temporal response and also to the EMG. The present invention offers the potential to better quantify a patient's motor ability and give diagnostic information. Moreover, the present invention consists of relatively low cost components, so as to reduce the overall cost.

Alternate Embodiment

Figure 39:
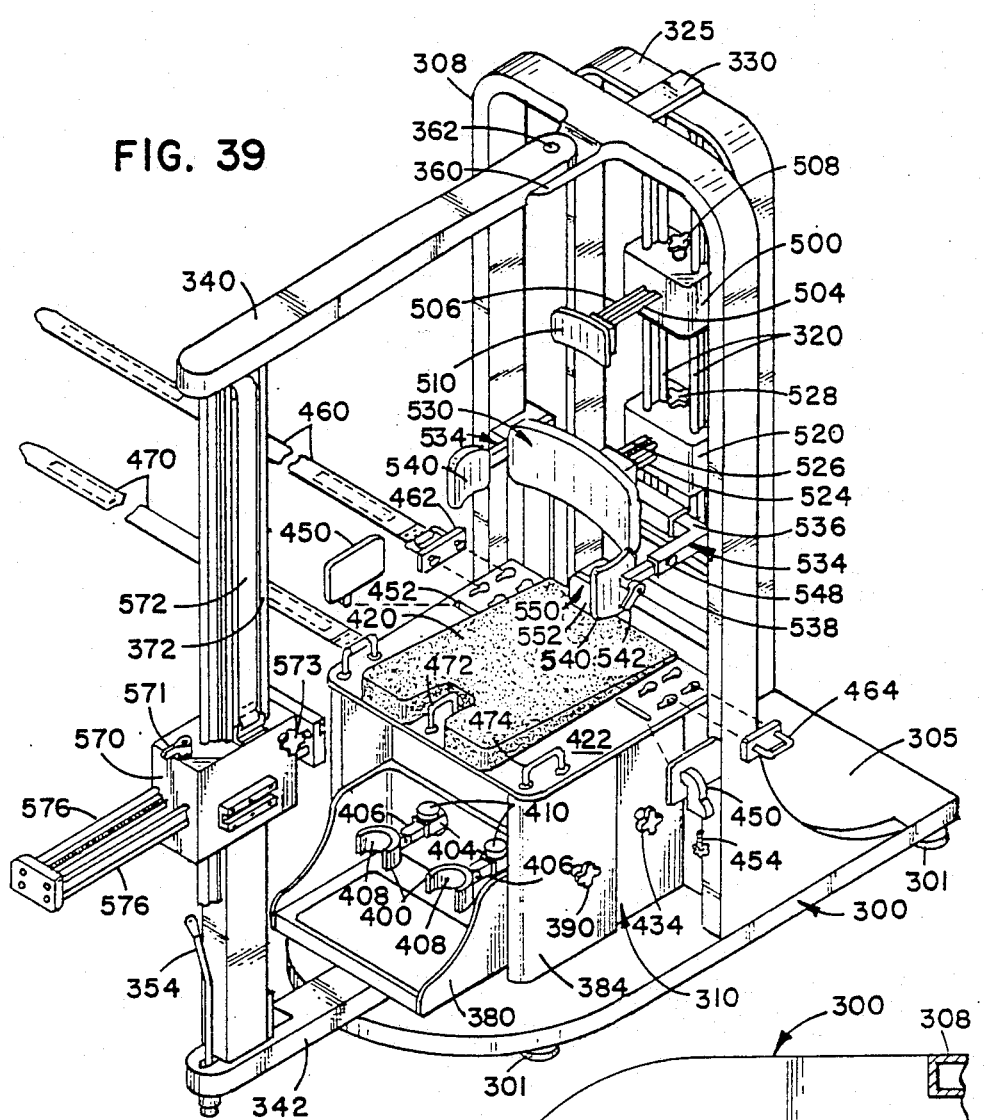
FIGS. 39–43 illustrate an alternate embodiment of the chair apparatus in accordance with the principles of the present invention.
Figure 43:
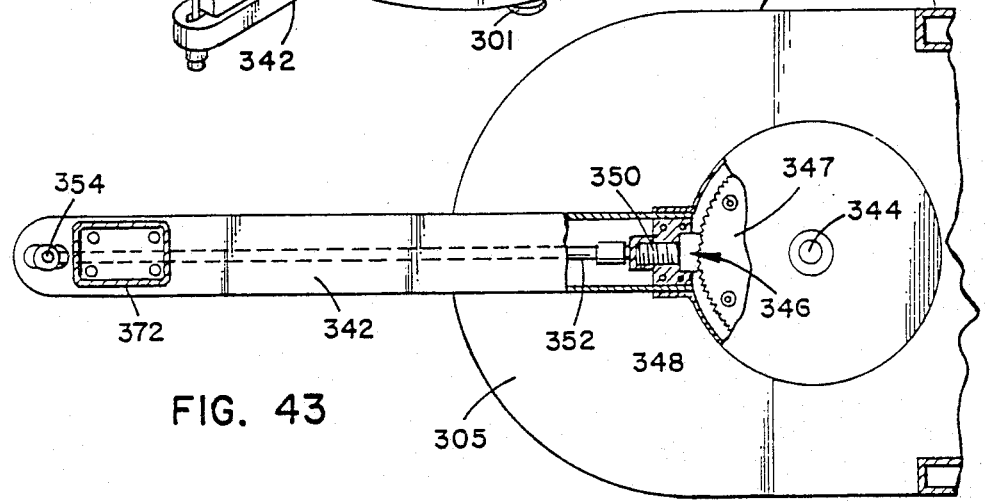
Figure 40:
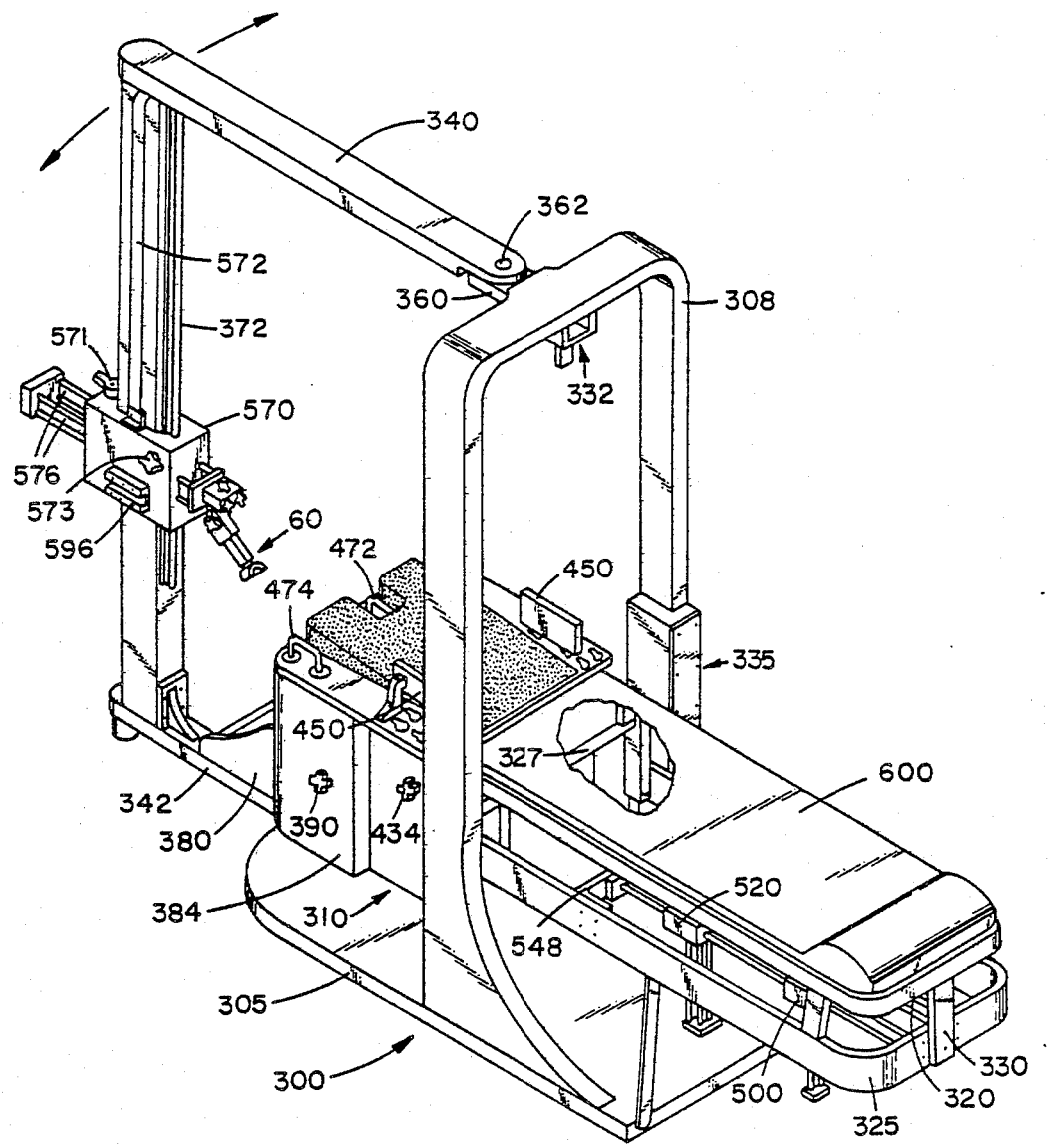
Figure 41:
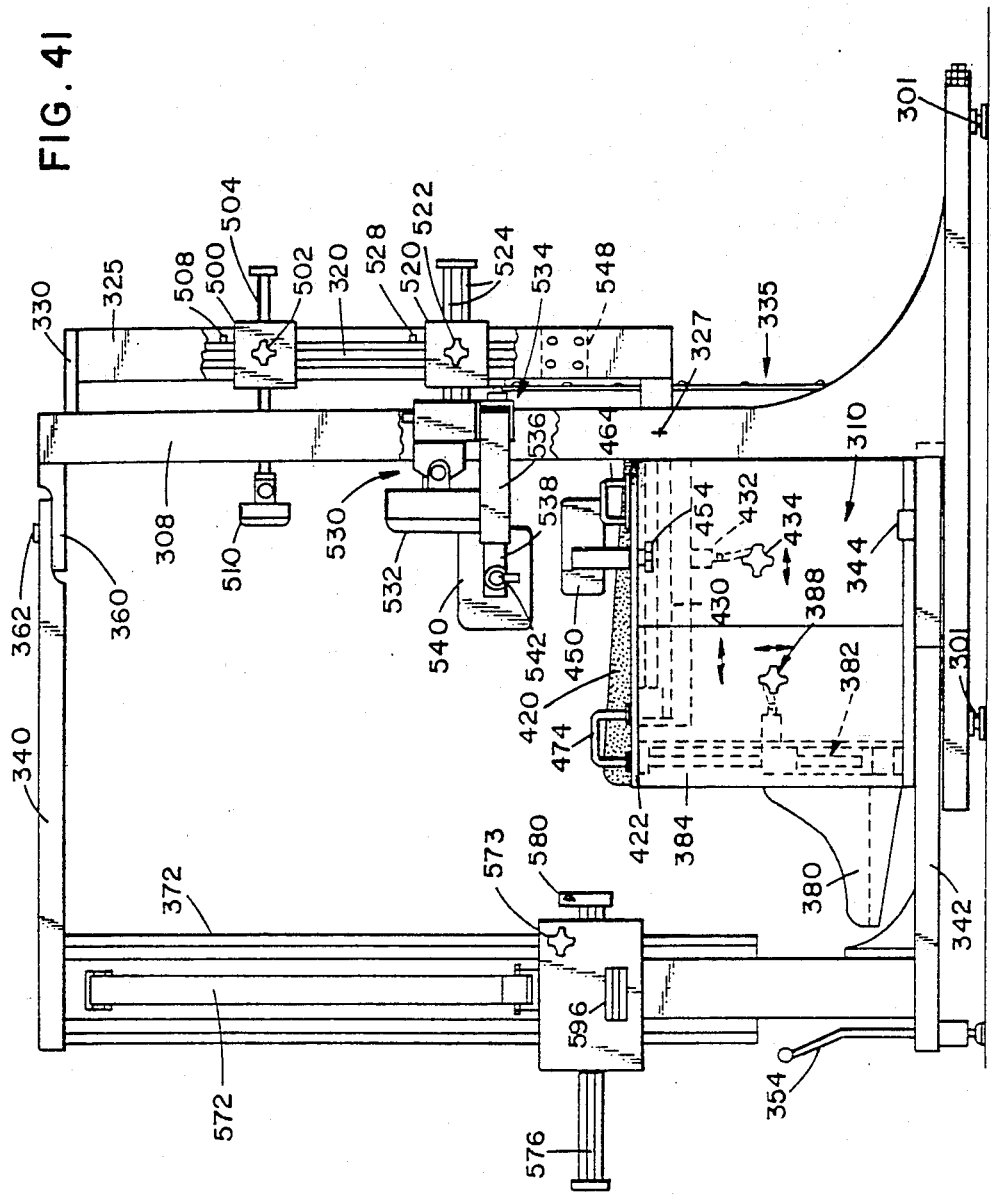
Figure 42:
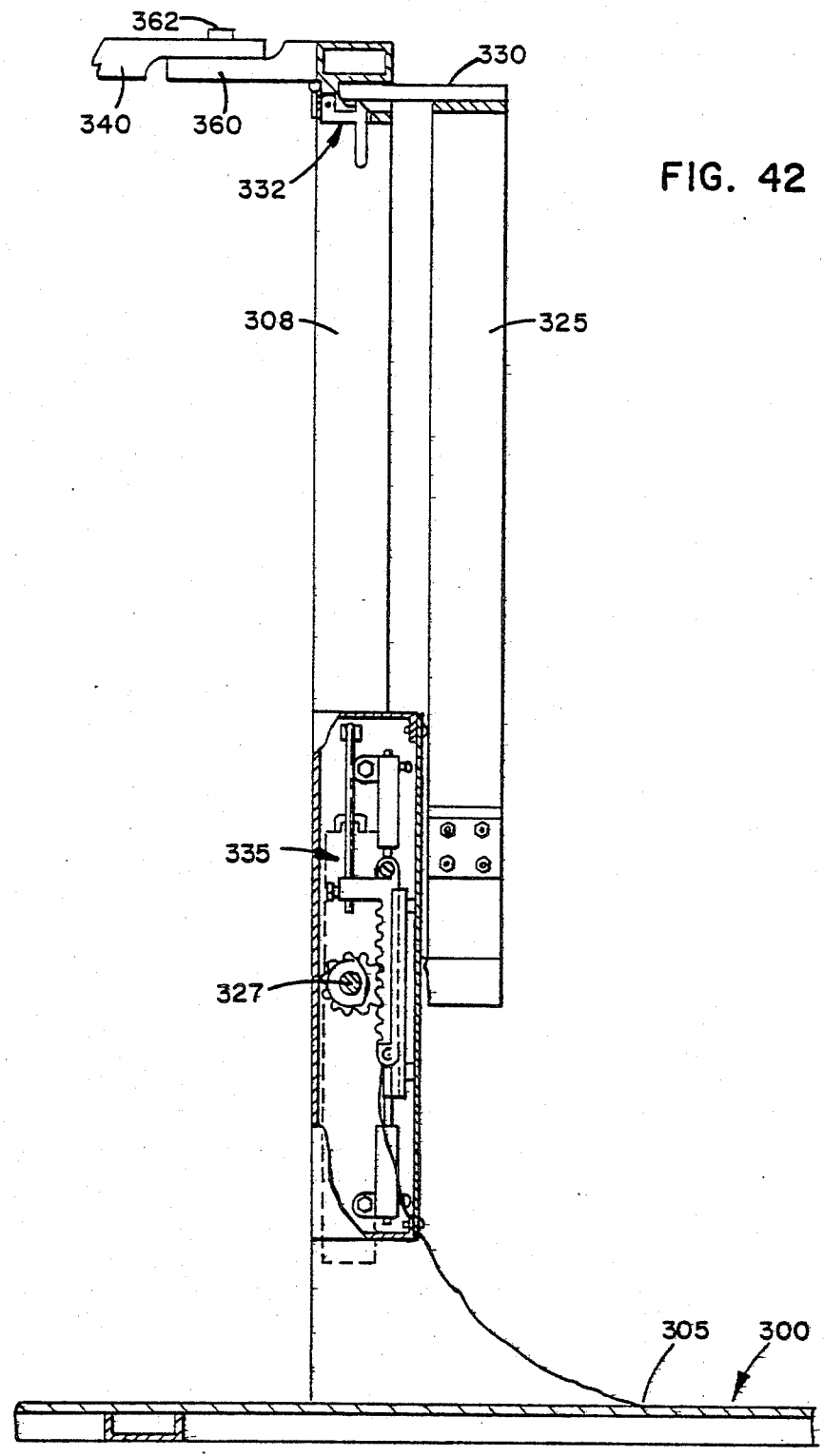

An alternate embodiment of the present invention is shown in FIGS. 39-43. The alternate chair apparatus includes a support frame structure 300 including four adjustable feet 301. Structure 300 includes a base member 305 on which is mounted a vertical frame member 308 and seat apparatus 310. A posterior track member 320 is provided and is mounted to a U-shaped frame member 325 which is mounted to frame member 308 at pivot points 327. Accordingly, frame member 325 may be disposed in a vertical position as shown in FIGS. 39, 41 and 42 or in a horizontal position as illustrated in FIG. 40. As best seen with reference to FIG. 42, frame 325 includes at the top thereof a latch member 330 by which it may be latched to a latching mechanism 332 at the top of frame member 308. Frame member 325 is pivotably linked to frame member 308 with a counterbalance mechanism 335 so that it may be pivoted up and down with steady moderate resistance so as to provide for a smooth transition between positions.

An anterior track 372 is also provided and is mounted between two horizontally extending members 340 and 342. Member 342 is connected to base 305 underneath seat apparatus 310 to pivot about axis 344. Preferably, as shown best in FIG. 43, member 342 includes a gear and pawl locking mechanism 346, including a gear member 347, a pawl 348, a spring 350, a spring loaded rod 352 and lever 354. Upper support member 340 is mounted from a tongue 360 extending from frame member 308 to pivot about axis 362. Accordingly, anterior track 372 may be rotated throughout a semicircular arc centered about axes 344 and 362. Preferably, track 372 may be moved throughout 190° of angle, 95° movement in either direction from the center position shown in the FIG. 43. Lever 354 is used to disengage pawl 348 from gear 347 when movement is desired, and to reengage and lock the assembly when the desired position has been attained.

As may be best seen with reference to FIGS. 39 and 41 seat apparatus 310 includes a foot rest portion 380 which is track mounted on a pair of parallel rails 382 (the right rail is not visible) mounted inside of housing 384. Foot support portion 380 is mounted to rails 382 with through carriages 386 and is preferably counterbalanced so that it may be moved up and down with a minimum of effort. A locking mechanism 388 is provided and includes a locking handle 390 via which carriage 386 may be locked into position onto rails 382 when foot rest portion 380 is at its desired height.

A pair of calf restraints 400 are provided and are each mounted to the back wall 402 of footrest portion 380 via a universal joint 404. Preferably, a minimum of 5° movement in any direction about the orthogonal axis of joint 404 is provided. Units 400 include telescoping portion 406 and cuff members 408 which are pivotably mounted to portions 406 for pivotable movement along a horizontal axis. Locking knobs 410 are provided to lock telescoping portions 406 in place.

Seat apparatus 310 also includes a seat pad 420, which is mounted on a platform 422. Platform 422 is in turn mounted on a carriage and track assembly 430 for backward and forward movement A locking mechanism 432 including a locking handle 434 is included to provide for the locking of platform 422 and seat 420 in a desired position.

On either side of seat 420 are hip stabilizer pads 450, which may be mounted in elongate slots 452 and secured in place with bolt members 454. Accordingly, pads 450 may be selectively installed and adjusted relative to the width of the chair. Also shown in an exploded away fashion is belt 460 which is coupled to a keyhole mounting member 462 which may be mounted to platform 422. On the other side a keyhole mounted loop member 464 is provided to provide an anchor point for belt 460, which preferably includes Velcro portions so that it may be readily secured in place around the patient. On the front end of platform 422 there is provided another belt 470, and a pair of loops 472 and 474 through which the belt may be looped in order to secure the patient's legs in place.

Track 320 is preferably a Thomson dual shaft rail system. Mounted for movement on rails 320 are carriages 500 and 520, each of which may be slidably adjusted along the rails and locked in position via locking mechanisms 502 and 522 respectively. Carriage 500 includes through the center thereof a linear bearing which receives track member 504 for horizontal movement back and forth therethrough. Track 504 preferably includes a gear tooth track 506 via which track 504 may be locked in place by pawl-ended locking member 508. A restraint pad or load cell unit 510 is pivotably mounted on the end of track 504.

Carriage 520 also includes linear bearings for receiving a pair of parallel-disposed tracks 524. The upper one of tracks 524 preferably includes a gear tooth center track 526 whereby the tracks may be locked in place with a pawl-ended locking member 528. Mounted on the end of tracks 524 is a thoracic stabilizer unit 530. Unit 530 preferably includes a main thoracic stabilizer pad 532 mounted for pivotable movement about a horizontal axis. Unit 530 further includes left and right trunk restraint assemblies 534 each of which include a first telescoping member 536 and a second telescoping member 538 whereby the position of pads 540 may be adjusted inwardly and outwardly and forwardly and backwardly, respectively. Pads 540 are preferably swivel mounted on the ends of telescoping members 538 and may be locked into place with swivel locks 542.

Mounted near the bottom of frame member 325 on a cross member 548 is a sacral support unit 550. Sacral support unit 550 is supported from cross member 548 with a universal joint, and includes a telescoping member (not shown) whereby its position may be adjusted. A pad 552 is supported from the end of the unit.

An anterior track carriage unit 570 is provided for vertical movement up and down track 372. Carriage 570 includes a counterbalancing mechanism, which comprises a weight and belt assembly, of which belt 572 is illustrated. Accordingly, carriage unit 570 may be moved up and down track 372 with a minimum of effort. Track 372 is preferably a Thomson dual shaft rail system. A latching mechanism 573 is provided to lock carriage 570 in a desired vertical position.

Carriage 570 includes a pair of parallel linear bearings extending therethrough. Parallel tracks 576 extend therethrough for horizontal back and forth movement relative to the carriage. A latching mechanism 571 is provided to lock tracks 576 in position. A mounting bracket 580 is connected to the inward ends of tracks 576, and includes a horizontal mounting track 582 to which stabilizing or load cell devices may be mounted. For instance, as shown in FIG. 40, a load cell cuff unit 600 may be mounted to brackets 582, to provide for muscle strength measurements involving the leg. Alternatively, an extension member may be connected to mount 582, and a thoracic stabilizer pad may be mounted thereto. Accordingly, carriage 570 may be adjusted to the appropriate height and tracks 576 adjusted inwardly to the appropriate position whereby the thorax may be stabilized. Further mounting brackets 596 are provided on either side of carriage 570, whereby further stabilizing or load measuring devices may be suspended.

As shown in FIG. 40, frame 325 may be positioned in a horizontal position. In such case a back support unit 600 is mounted to the frame as shown in FIG. 40. Accordingly, the patient may lay back onto unit 600 where such position is required for testing, for instance for hip flexion, extension, abduction, adduction.

The positioning of load cells and stabilization devices on the various carriages and tracks of the alternate embodiment chair is preferably accomplished in the same general manner as set forth above with respect to the first-described embodiment of the present invention. Similarly, load cell operation is also generally the same whereby measurements may be obtained.

It is to be understood that even though numerous characteristics and advantages of various embodiments of the present invention have been set forth in the foregoing description, together with details of the structure and function of various embodiments of the invention, this disclosure is illustrative only and changes may be made in detail, especially in matters of shape, size and arrangement of parts, within the principles of the present invention, to the full extent indicated by the broad general meaning of the terms in which the appended claims are expressed.

What is claimed is:

1. An isometric muscle strength testing chair apparatus for measuring the isometric muscle strength of any of a plurality of muscle groups in a human subject's body, the apparatus comprising:
   (a) a support frame;
   (b) transducer means interconnected to the support frame for measuring the force exerted by the muscle groups selected for testing, the transducer means remaining substantially stationary while the muscle groups selected for testing exert a force thereon so as to provide for isometric strength testing;
   (c) vertical track means for adjustably positioning the transducer means in association with the muscle groups selected for testing in front and on both sides of the subject's body, the vertical track means including support block means slidably mounted on the vertical track means for supporting horizontal track means, the horizontal track means supporting the transducer means for adjustable movement of the transducer means substantially at right angles to the vertical track means on which the support block means is slidably mounted;
   (d) stabilization means for selectively engaging and immobilizing various parts of the human subject's body as required to enable the muscle groups selected for testing to be tested while isolated from the other muscle groups of the human subject's body;
   (e) a seat assembly mounted on the support frame;
   (f) a back support assembly slidably mounted on a vertical back support track means mounted on the support frame; and
   (g) a foot rest assembly mounted on the support frame.

2. An apparatus in accordance with claim 1, wherein the foot rest assembly is vertically adjustable and the seat assembly is horizontally adjustable in a backward and forward direction with respect to the human subject's body.

3. An apparatus in accordance with claim 1, wherein the transducer means includes load cell means for converting the force exerted on the transducer means by the muscle groups selected for testing to an electrical signal representative of the force exerted by the muscle groups selected for testing on the load cell means.

4. An isometric muscle strength testing chair apparatus for measuring the isometric muscle strength of any of a plurality of muscle groups in a human subject's body, the apparatus comprising:
   (a) a support frame;
   (b) transducer means interconnected to the support frame for measuring the force exerted by the muscle groups selected for testing, the transducer means remaining substantially stationary while the muscle groups selected for testing exert a force thereon so as to provide for isometric strength testing;
   (c) track means for adjustably positioning the transducer means in association with the muscle groups selected for testing, the track means including T-block means slidably mounted on the track means for supporting the transducer means, the track means including two cylindrical rods in parallel relationship, the T-block means including secondary track means slidably supported by the T-block means for movement substantially at right angles to the track on which the T-block means is slidably mounted, the T-block means including means for slidably receiving the two cylindrical rods;
   (d) stabilization means for selectively engaging and immobilizing various parts of the human subject's body as required to enable the muscle groups selected for testing to be tested while isolated from the other muscle groups of the human subject's body;
   (e) a seat assembly mounted on a support frame; and
   (f) a foot rest assembly mounted on the support frame.

5. An apparatus in accordance with claim 4, wherein the transducer means includes load cell means for outputting an electrical signal corresponding to the quantity of force applied to the load cell means by the muscle groups selected for testing.

6. An apparatus in accordance with claim 4, wherein the T-block means further includes latch means for releasably securing the T-block means in position on the cylindrical rods of the track means, the latch means including a split locking collar means positioned about one of the cylindrical rods for engaging the cylindrical rod on being operated on by an external handle member interconnected to the split locking collar means, the split locking collar means being interconnected to anchor means for anchoring the split locking collar means whereby the split locking collar means is made to wedge against the cylindrical rod as the cylindrical rod is moved relative to the split locking collar means in one direction or another.

7. An isometric muscle strength testing chair apparatus for measuring the isometric muscle strength of any of a plurality of muscle groups in a human subject's body, the apparatus comprising:
  (a) a support frame;
  (b) transducer means interconnected to the support frame for measuring the force exerted by the muscle groups selected for testing, the transducer means remaining substantially stationary while the muscle groups selected for testing exert a force thereon so as to provide for isometric strength testing;
  (c) vertical track means for adjustably positioning the transducer means in association with the muscle groups selected for testing;
  (d) stabilization means for selectively engaging and immobilizing various parts of the human subject's body as required to enable the muscle groups selected for testing to be tested while isolated from the other muscle groups of the human subject's body;
  (e) a seat assembly mounted on the support frame; and
  (f) pivot mount means for supporting the vertical track means for pivotal movement through an arc about a vertical axis centered proximate the seat assembly.

8. An apparatus in accordance with claim 7, further comprising a foot rest assembly mounted on the support frame.

9. An apparatus in accordance with claim 8, wherein the foot rest assembly is vertically adjustable and the seat assembly is horizontally adjustable in a backward and forward direction with respect to the human subject's body.

10. An apparatus in accordance with claim 7, wherein the transducer means includes load cell means for converting the force exerted on the transducer means by the muscle groups selected for testing to an electrical signal representative of the force exerted by the muscle groups selected for testing on the load cell means.

11. An apparatus in accordance with claim 7, the vertical track means including support block means slidably mounted on the vertical track means for supporting horizontal track means, the horizontal track means supporting the transducer means for adjustable movement of the transducer means substantially at right angles to the vertical track means on which the support block means is slidably mounted.

12. An apparatus in accordance with claim 7, further comprising a back support assembly slidably mounted on vertical back support track means mounted on the support frame.

13. An apparatus in accordance with claim 7, wherein the vertical track means is interconnected to the pivot mount means by a horizontally extending member, the pivot mount means including a gear and pawl locking means for pivotally connecting the horizontally extending member to the chair apparatus.

* * * * *

UNITED STATES PATENT AND TRADEMARK OFFICE
CERTIFICATE OF CORRECTION

PATENT NO.  : 4,702,108
DATED       : October 27, 1987
INVENTOR(S) : Amundsen et al.

It is certified that error appears in the above-identified patent and that said Letters Patent is hereby corrected as shown below:

Column 12, line 19, "cur vilinear" should be --curvilinear--.

Column 13, line 16, "supportes" should be --supports--.

Column 20, line 45, after "track" insert --means--.

Signed and Sealed this

Twenty-first Day of November, 1989

Attest:

JEFFREY M. SAMUELS

*Attesting Officer*      *Acting Commissioner of Patents and Trademarks*